(12) United States Patent
Robson et al.

(10) Patent No.: US 9,110,063 B2
(45) Date of Patent: Aug. 18, 2015

(54) ASSAY METHODS FOR THE DETERMINATION OF FKBPL EXPRESSION LEVEL IN THE CONTEXT OF BREAST CANCER

(75) Inventors: Tracy Robson, Belfast (GB); David Hirst, Belfast (GB); Hayley McKeen, Carrickfergus (GB); Christopher Byrne, Lifford (IE)

(73) Assignee: The Queen's University of Belfast, Belfast (GB)

( * ) Notice: Subject to any disclaimer, the term of this patent is extended or adjusted under 35 U.S.C. 154(b) by 11 days.

(21) Appl. No.: 13/265,223

(22) PCT Filed: May 19, 2010

(86) PCT No.: PCT/GB2010/050819
§ 371 (c)(1),
(2), (4) Date: Nov. 30, 2011

(87) PCT Pub. No.: WO2010/133880
PCT Pub. Date: Nov. 25, 2010

(65) Prior Publication Data
US 2012/0115830 A1 May 10, 2012

(30) Foreign Application Priority Data
May 19, 2009 (GB) .................................. 0908589.5

(51) Int. Cl.
*G01N 33/53* (2006.01)
*C12Q 1/68* (2006.01)
*A61P 35/00* (2006.01)
*G01N 33/573* (2006.01)
*G01N 33/574* (2006.01)

(52) U.S. Cl.
CPC ............ *G01N 33/573* (2013.01); *C12Q 1/6886* (2013.01); *G01N 33/57415* (2013.01); *C12Q 2600/106* (2013.01); *C12Q 2600/118* (2013.01); *C12Q 2600/158* (2013.01); *G01N 2333/99* (2013.01)

(58) Field of Classification Search
None
See application file for complete search history.

(56) References Cited

U.S. PATENT DOCUMENTS

2004/0002067 A1* 1/2004 Erlander et al. ................. 435/6
2009/0047689 A1 2/2009 Kolman et al.

FOREIGN PATENT DOCUMENTS

| CN | 101432437 A | 5/2009 |
|---|---|---|
| WO | WO-2005/118875 A2 | 12/2005 |
| WO | WO-2006/135886 A2 | 12/2006 |
| WO | WO-2007/141533 A2 | 12/2007 |

OTHER PUBLICATIONS

McKeen et al (Breast Cancer Research, May 13, 2008, 10(Suppl 2):P1).*
Miller et al (Journal of Clinical Oncology, 2009, 27:1382-1387, published online Feb. 17, 2009).*
Adapt, Paterson Institute for Cancer Research, probesets for FKBPL, printed Dec. 31, 2013.*
Adapt, Paterson Institute for Cancer Research, probesets for estrogen receptor (ESR1), printed Jan. 3, 2013.*
Adapt, Paterson Institute for Cancer Research, probesets for progesterone receptor (PGR), printed Jan. 3, 2013.*
Loi et al (BMC Genomics, 2008, 9:239, internet pp. 1-12; published online May 22, 2008).*
Frasor et al (Cancer Research, 2006, 66:7334-7340).*
Fisher et al (The Lancet, 1999, 353:1993-2000).*
Cuzick et al (JNCI, 2007, 99: 272-282).*
Murphy et al (Clinical Cancer Research, 2004, 10:5902-5906).*
O'Brien, Sallyann L. et al., "CENP-F expression is associated with poor prognosis and chromosomal instablilty in patients with primary breast cancer", Int. J. Cancer: 120, 2007, pp. 1434-1443.
Robson, T.A. et al., "Gene regulation by low-dose ionizing radiation in a normal human lung epithelial cell line", Biochemical Society Transactions, vol. 25, 1997, pp. 335-342.
Jascur, Thomas et al., "Regulation of p21WAF1/CIP1 Stability by WISp39, a Hsp90 Binding TPR Protein", Molecular Cell, vol. 17, Jan. 21, 2005, pp. 237-249.
Sieuwerts, Anieta M. et al., "How ADAM-9 and ADAM-11 Differentially From Estrogen Receptor Predict Response to Tamoxifen Treatment in Patients with Recurrent Breast Cancer: a Retrospective Study", Clin Cancer Res 2005; 11:7311-7321, Oct. 20, 2005.
McKeen et al., FKBLP Regulates Receptor Signaling and Determines Response to Endocrine Therapy, Cancer Res.; 70(3); pp. 1090-1100 (2010).
Giry, Murielle, "International Search Report" for PCT/GB2010/050819, as mailed Oct. 1, 2010, 5 pages.
McKeen, H.D., et al., "A novel FK506-like binding protein interacts with the glucocorticoid receptor and regulates steroid receptor signaling", Endocrinology, vol. 149, No. 11, Nov. 1, 2008, pp. 5724-5734.
Ward, B.K., et al., "Expression of the estrogen receptor-associated immunophilins, cyclophilin 40 and FKBP52, in breast cancer", Breast Cancer Res. Treatment, vol. 58, No. 3, Dec. 1, 1999, pp. 267-280.
Han, W., et al., "Genomic alterations identified by array comparative genomic hybridization as prognostic markers in tamoxifen-treated estrogen receptor-positive breast cancer", BMC Cancer, vol. 6, No. 1, Apr. 12, 2006, pp. 92-104.
McKeen, H.D., et al., "FKBPL regulates estrogen receptor signaling and determines response to endocrine therapy", Cancer Res., vol. 70, No. 3, Feb. 1, 2010, pp. 1090-1100.
Jascur, Thomas, et al., Regulation of p21WAF1/CIP1 Stability by WISp39, a Hsp90 Binding TPR Protein, Molecular Cell, vol. 17, Jan. 21, 2005, pp. 237-249.
Abukhdeir, Abde, et al., "Tamoxifen-stimulated growth of breast cancer due to p21 loss", Proceedings of the National Academy of Sciences of the United States of America 105 (2008), pp. 288-293.

* cited by examiner

Primary Examiner — Laura B Goddard
(74) Attorney, Agent, or Firm — Winstead PC

(57) ABSTRACT

Disclosed are methods that employ FKBPL as a marker for a subject's sensitivity to endocrine therapies in the treatment of cancers, and as a predictive marker of cancer progression and disease free survival in relation to hormone responsive cancers.

11 Claims, 14 Drawing Sheets

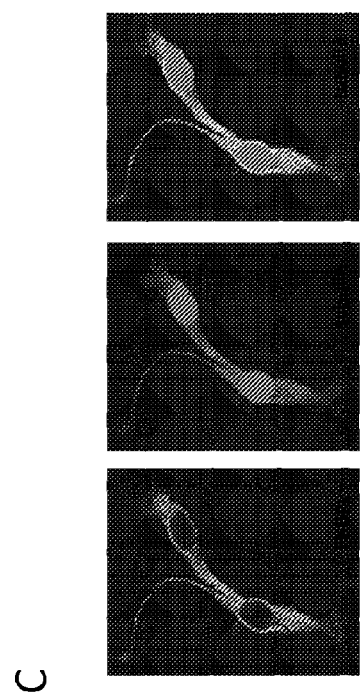
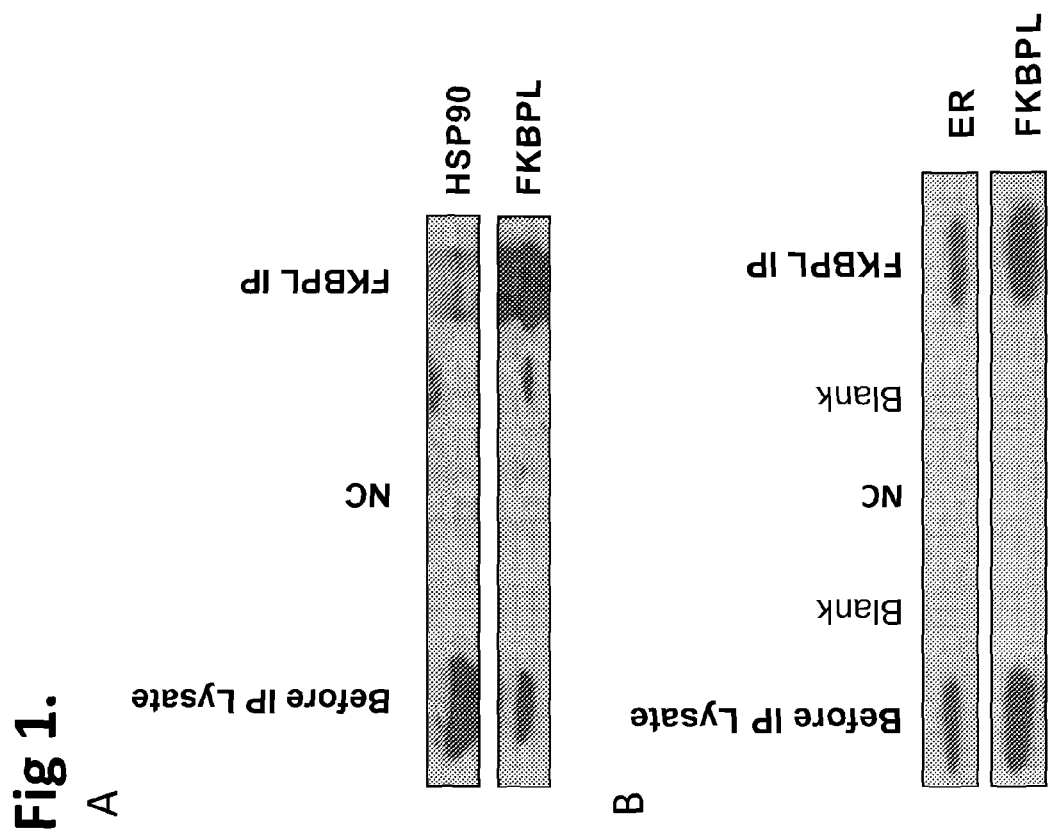
Fig 1.

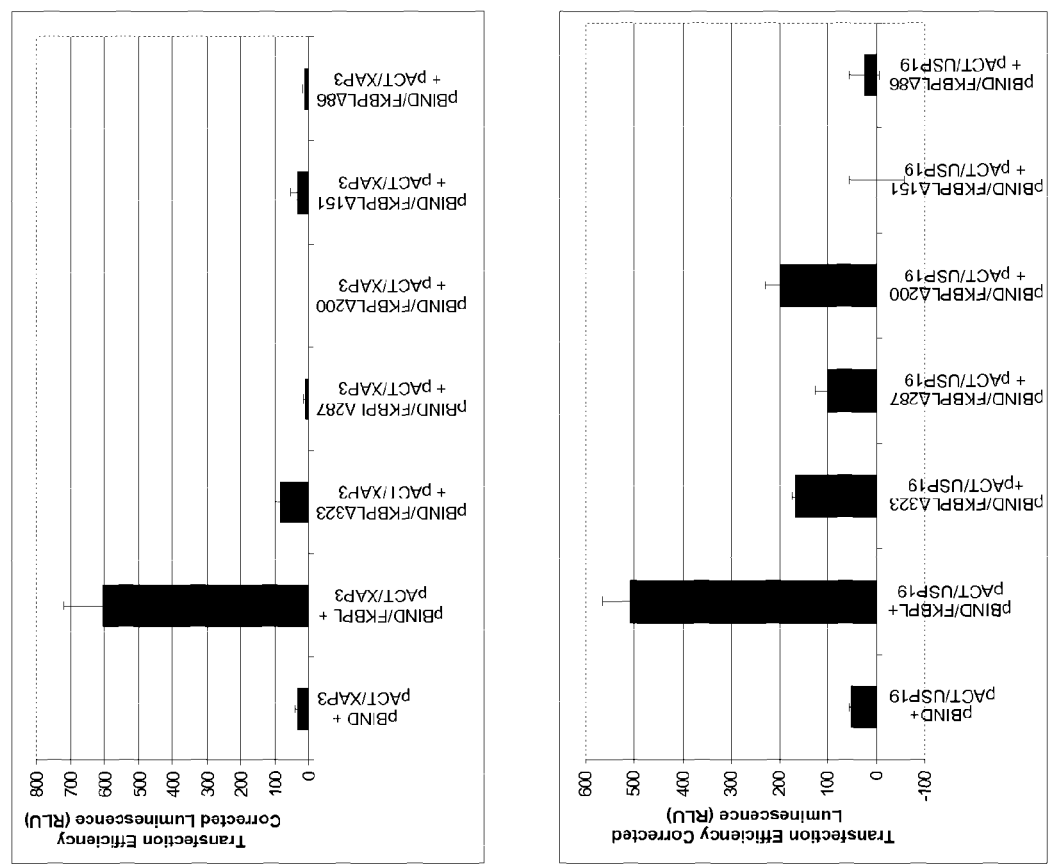
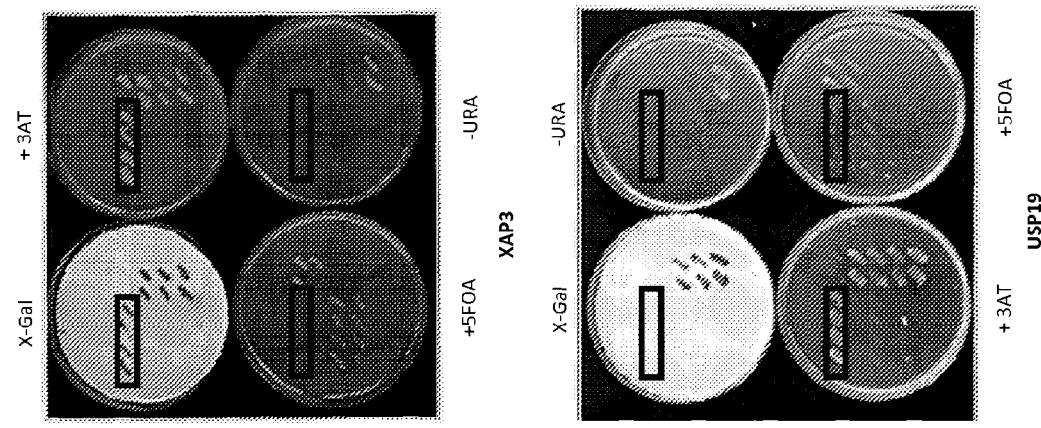
Fig 2.

Fig 4.
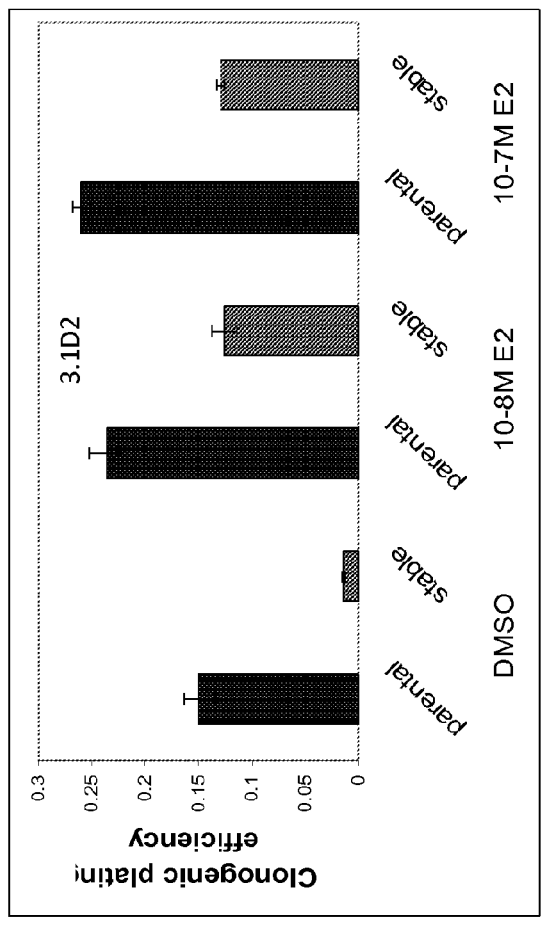
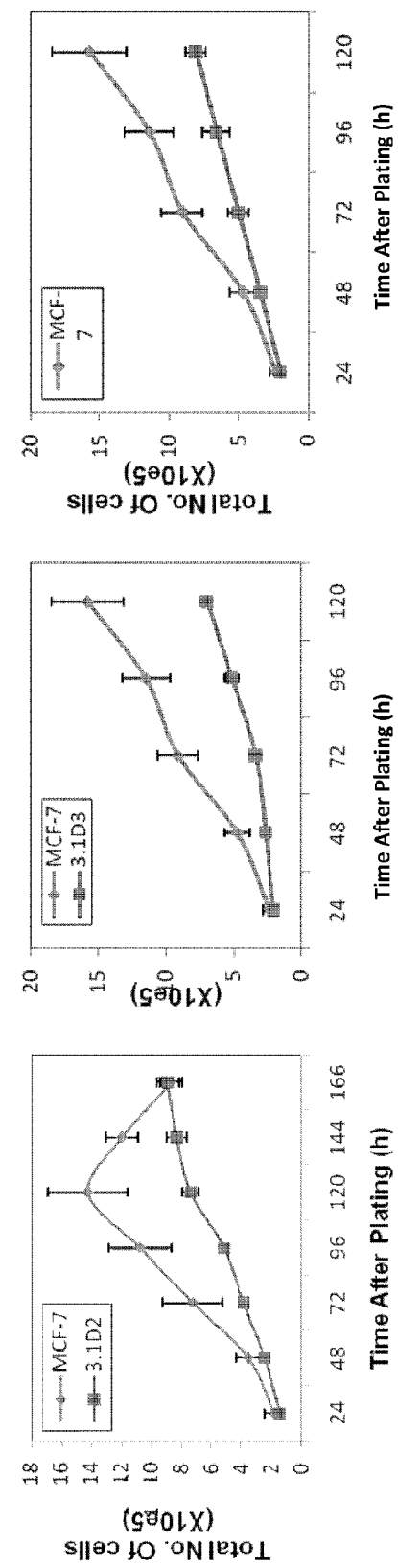

A

SEQUENCE LISTING

```
<160> NUMBER OF SEQ ID NOS: 5

<210> SEQ ID NO 1
<211> LENGTH: 1087
<212> TYPE: DNA
<213> ORGANISM: Homo sapiens

<400> SEQUENCE: 1
atggagacgc caccagtcaa tacaattgga gaaaaggaca cctctcagcc gcaacaagag      60
tgggaaaaga accttcggga gaaccttgat tcagttattc agattaggca gcagccccga     120
gaccctccta ccgaaacgct tgagctggaa gtaagcccag atccagccag ccaaattcta     180
gagcatactc aaggagctga aaaactggtt gctgaacttg aaggagactc tcataagtct     240
catggatcaa ccagtcagat gccagaggcc cttcaagctt ctgatctctg gtactgcccc     300
gatgggagct ttgtcaagaa gatcgtaatc cgtggccatg gcttggacaa acccaaacta     360
ggctcctgct gccgggtact ggctttgggg tttcctttcg gatcagggcc gccagagggc     420
tggacagagc taactatggg cgtagggcca tggagggagg aaacttgggg ggagctcata     480
gagaaatgct tggagtccat gtgtcaaggt gaggaagcag agcttcagct gcctgggcac     540
tctggacctc ctgtcaggct cacactggca tccttcactc aaggccgaga ctcctgggag     600
```

```
ctggagacta gcgagaagga agccctggcc agggaagaac gtgcaagggg cacagaacta    660
tttcgagctg ggaaccctga aggagctgcc cgatgctatg gacgggctct tcggctgctc    720
ctgactttac ccccacctgg ccctccagaa cgaactgtcc ttcatgccaa tctggctgcc    780
tgtcagttgt tgctagggca gcctcagttg cagcccaga gctgtgaccg ggtgttggag     840
cgggagcctg gccatttaaa ggccttatac cgaagggggg ttgcccaggc tgcccttggg    900
aacctggaaa aagcaactgc tgacctcaag aaggtgctgg cgatagatcc caaaaaccgg    960
gcagcccagg aggaactggg gaaggtggtc attcagggga agaaccagga tgcagggctg   1020
gctcagggtc tgcgcaagat gtttggctga ttaaaagtta aaccttaaaa gagaaaaaaa   1080
aaaaaaa                                                             1087
```

<210> SEQ ID NO 2
<211> LENGTH: 349
<212> TYPE: PRT
<213> ORGANISM: Homo sapiens

<400> SEQUENCE: 2

```
Met Glu Thr Pro Pro Val Asn Thr Ile Gly Glu Lys Asp Thr Ser Gln
1               5                   10                  15

Pro Gln Gln Glu Trp Glu Lys Asn Leu Arg Glu Asn Leu Asp Ser Val
            20                  25                  30

Ile Gln Ile Arg Gln Gln Pro Arg Asp Pro Thr Glu Thr Leu Glu
        35                  40                  45

Leu Glu Val Ser Pro Asp Pro Ala Ser Gln Ile Leu Glu His Thr Gln
50                  55                  60

Gly Ala Glu Lys Leu Val Ala Glu Leu Glu Gly Asp Ser His Lys Ser
65                  70                  75                  80

His Gly Ser Thr Ser Gln Met Pro Glu Ala Leu Gln Ala Ser Asp Leu
                85                  90                  95

Trp Tyr Cys Pro Asp Gly Ser Phe Val Lys Lys Ile Val Ile Arg Gly
            100                 105                 110

His Gly Leu Asp Lys Pro Lys Leu Gly Ser Cys Cys Arg Val Leu Ala
        115                 120                 125

Leu Gly Phe Pro Phe Gly Ser Gly Pro Pro Glu Gly Trp Thr Glu Leu
    130                 135                 140

Thr Met Gly Val Gly Pro Trp Arg Glu Glu Thr Trp Gly Glu Leu Ile
145                 150                 155                 160

Glu Lys Cys Leu Glu Ser Met Cys Gln Gly Glu Glu Ala Glu Leu Gln
                165                 170                 175

Leu Pro Gly His Ser Gly Pro Pro Val Arg Leu Thr Leu Ala Ser Phe
            180                 185                 190

Thr Gln Gly Arg Asp Ser Trp Glu Leu Glu Thr Ser Glu Lys Glu Ala
        195                 200                 205

Leu Ala Arg Glu Glu Arg Ala Arg Gly Thr Glu Leu Phe Arg Ala Gly
    210                 215                 220

Asn Pro Glu Gly Ala Ala Arg Cys Tyr Gly Arg Ala Leu Arg Leu Leu
225                 230                 235                 240

Leu Thr Leu Pro Pro Pro Gly Pro Pro Glu Arg Thr Val Leu His Ala
                245                 250                 255

Asn Leu Ala Ala Cys Gln Leu Leu Leu Gly Gln Pro Gln Leu Ala Ala
            260                 265                 270

Gln Ser Cys Asp Arg Val Leu Glu Arg Glu Pro Gly His Leu Lys Ala
```

```
                275                 280                 285
Leu Tyr Arg Arg Gly Val Ala Gln Ala Ala Leu Gly Asn Leu Glu Lys
        290                 295                 300

Ala Thr Ala Asp Leu Lys Lys Val Leu Ala Ile Asp Pro Lys Asn Arg
305                 310                 315                 320

Ala Ala Gln Glu Glu Leu Gly Lys Val Val Ile Gln Gly Lys Asn Gln
                325                 330                 335

Asp Ala Gly Leu Ala Gln Gly Leu Arg Lys Met Phe Gly
        340                 345

<210> SEQ ID NO 3
<211> LENGTH: 1087
<212> TYPE: DNA
<213> ORGANISM: Homo sapiens

<400> SEQUENCE: 3
atggagacgc caccagtcaa tacaattgga gaaaaggaca cctctcagcc gcaacaagag      60
tgggaaaaga accttcggga gaaccttgat tcagttattc agattaggca gcagccccga     120
gaccctccta ccgaaacgct tgagctggaa gtaagcccag atccagccag ccaaattcta     180
gagcatactc aaggagctga aaaactggtt gctgaacttg aaggagactc tcataagtct     240
catggatcaa ccagtcagat gccagaggcc cttcaagctt ctgatctctg gtactgcccc     300
gatgggagct ttgtcaagaa gatcgtaatc cgtggccatg gcttggacaa acccaaacta     360
ggctcctgct gccgggtact ggctttgggg tttccttttcg gatcagggcc gccagagggc     420
tggacagagc taactatggg cgtagggcca tggaggagg aaacttgggg ggagctcata     480
gagaaatgct tggagtccat gtgtcaaggt gaggaagcag agcttcagct gcctgggcac     540
actggacctc ctgtcgggct cacactggca tccttcactc aaggccgaga ctcctgggag     600
ctggagacta gcgagaagga agccctggcc agggaagaac gtgcaagggg cacagaacta     660
tttcgagctg gaaccctga aggagctgcc cgatgctatg gacgggctct tcggctgctc     720
ctgactttac ccccacctgg ccctccagaa cgaactgtcc ttcatgccaa tctggctgcc     780
tgtcagttgt tgctagggca gcctcagttg cagcccagag ctgtgaccg ggtgttggag     840 cgggagcctg ccatttaaa ggccttatac cgaagggggg ttgcccaggc tgcccttggg     900
aacctggaaa aagcaactgc tgacctcaag aaggtgctgg cgatagatcc aaaaaccgg     960 gcagcccagg aggaactggg gaaggtggtc attcagggga gaaccagga tgcagggctg    1020 gctcagggtc tgcgcaagat gtttggctga ttaaaagtta aaccttaaaa gagaaaaaaa    1080
aaaaaaa                                                              1087

<210> SEQ ID NO 4
<211> LENGTH: 349
<212> TYPE: PRT
<213> ORGANISM: Homo sapiens

<400> SEQUENCE: 4

Met Glu Thr Pro Pro Val Asn Thr Ile Gly Glu Lys Asp Thr Ser Gln
1               5                   10                  15

Pro Gln Gln Glu Trp Glu Lys Asn Leu Arg Glu Asn Leu Asp Ser Val
            20                  25                  30

Ile Gln Ile Arg Gln Gln Pro Arg Asp Pro Pro Thr Glu Thr Leu Glu
        35                  40                  45

Leu Glu Val Ser Pro Asp Pro Ala Ser Gln Ile Leu Glu His Thr Gln
    50                  55                  60
```

```
Gly Ala Glu Lys Leu Val Ala Glu Leu Glu Gly Asp Ser His Lys Ser
 65                  70                  75                  80

His Gly Ser Thr Ser Gln Met Pro Glu Ala Leu Gln Ala Ser Asp Leu
                 85                  90                  95

Trp Tyr Cys Pro Asp Gly Ser Phe Val Lys Lys Ile Val Ile Arg Gly
            100                 105                 110

His Gly Leu Asp Lys Pro Lys Leu Gly Ser Cys Cys Arg Val Leu Ala
            115                 120                 125

Leu Gly Phe Pro Phe Gly Ser Gly Pro Pro Glu Gly Trp Thr Glu Leu
130                 135                 140

Thr Met Gly Val Gly Pro Trp Arg Glu Glu Thr Trp Gly Glu Leu Ile
145                 150                 155                 160

Glu Lys Cys Leu Glu Ser Met Cys Gln Gly Glu Glu Ala Glu Leu Gln
                165                 170                 175

Leu Pro Gly His Thr Gly Pro Pro Val Gly Leu Thr Leu Ala Ser Phe
            180                 185                 190

Thr Gln Gly Arg Asp Ser Trp Glu Leu Glu Thr Ser Glu Lys Glu Ala
            195                 200                 205

Leu Ala Arg Glu Glu Arg Ala Arg Gly Thr Glu Leu Phe Arg Ala Gly
210                 215                 220

Asn Pro Glu Gly Ala Ala Arg Cys Tyr Gly Arg Ala Leu Arg Leu Leu
225                 230                 235                 240

Leu Thr Leu Pro Pro Pro Gly Pro Pro Glu Arg Thr Val Leu His Ala
                245                 250                 255

Asn Leu Ala Ala Cys Gln Leu Leu Leu Gly Gln Pro Gln Leu Ala Ala
            260                 265                 270

Gln Ser Cys Asp Arg Val Leu Glu Arg Glu Pro Gly His Leu Lys Ala
            275                 280                 285

Leu Tyr Arg Arg Gly Val Ala Gln Ala Ala Leu Gly Asn Leu Glu Lys
290                 295                 300

Ala Thr Ala Asp Leu Lys Lys Val Leu Ala Ile Asp Pro Lys Asn Arg
305                 310                 315                 320

Ala Ala Gln Glu Glu Leu Gly Lys Val Val Ile Gln Gly Lys Asn Gln
                325                 330                 335

Asp Ala Gly Leu Ala Gln Gly Leu Arg Lys Met Phe Gly
            340                 345

<210> SEQ ID NO 5
<211> LENGTH: 2281
<212> TYPE: DNA
<213> ORGANISM: Homo sapiens

<400> SEQUENCE: 5
tttcttgatg aaggaggact tgaaaggcaa tgatggatgt gaaaggaaag gtaaagagaa      60
gcctcaggta gtcacccaag ggacagggcc ggttggagag agagtcccga ggttttatcc     120
tggagaacac cctgtactga atgagctctg aacataaaga tagttagcat aggagggcct     180
gaagtctcca gataaaaggc tgctgccact atcatttacc acgacctctg ccattctcca     240
ctctattgtc atccgccccc agtctccatt ccaggacttc tctacacttt gactttttgt     300
ttgtttgttt gtttgtttga gacggagtct tgcgctgtcg cccaggctgg agcgcagtgg     360
cacgatcttg gctcaccgca agctccgcct tccgggttca tgccattctc ctgcctcagc     420
ctcccgggta gctgggacta taggtgcccg ccaccacgcc cagctaattt tttgtatttt     480
```

```
tagtagagac gggtttcac catgttgtcc aggctggtct cgaacccctg acctcaagtg    540
atccccgc cgccccgccc cctcccccg cccgccccc cccgccgcc tcggcctccc       600
aaattgctgg gattacaggc gtgcgcgatg cccggctttt tatttattta tttatttatt  660
tttgaggcgg gaatcttgct ctgtcgccag gctggattgc agtggcacca tctcggctca  720
ctgcaacctc cgactccctg gttcaagcga ttctcccacc tcagcctccc aagtagctgg  780
gattacaggc acacgccacc atgcccagct aactttttgt attttagta gagacgagat   840
ttcaccatgt tgccaggatg gtctcgatca cctgacctcg tgatccgccc acctcagcct  900
cccagagtct cagttgccaa agctggagtg caatggcgcg atctcggctc actgcaacct  960
ccgcttccca ggtaagccat tctcctgcct cagcctcctg ggtagctggg atataggcgc 1020
ccgccatcac gccgagctat ttttgcattt ttagtagaga cggggtttca ccatgttggc 1080
caggctggtc ttgaactcct gacctcaacc tcccaaagtg ctgggattac aggcgtgagc 1140
caccgcgccc ggcccacctt tttttttttt tttttttttt tttttgttt gagacggagt  1200
ctctagtctc gctctgtcgc ccaggctgga gtgcaatggc gtgatctcgg ctcactgcaa 1260
cgtctgtctc ccgggttcaa gcgattctcc tgtttcagcc ttccgagtag ttgggattac 1320
aggcgcgcgc caccatgacc tactaatttt tgtatttta gtagagacag ggtctcacca  1380
tgttggccca ctttgactct tgagcagcct ggccagcccg accgcgccaa attctgttcg 1440
attctgccta gttcggttgc tctggcctag ttcagttgct aaggcctgga gcttcatggt 1500
tgcggaggaa atgatgtcac gttcaatagg cgggctaacc agattcctcc cttctcccga 1560
ttggctgcca ggaatttgac tagattcgga gtctcgcggg ctccagggtt agttgtcagt 1620
atctttccca gttgttccgc cccctacccc cttggctgcc aggaatttga ctagattcgg 1680
agtctcgcgg gctccagggt tagttgtcag tatctttccc agttgttccg cccctaccc  1740
ccgcctcccg caccgcgccc ctctccggct gccctctccg cgtggggcaa ggctccgagg 1800
gcagcattca gtagccattt agctttggaa ggagaggtga ttcgaatggc ccggctcctc 1860
ctgtcaccat gctaggcact ttggccgcgc aggtacttat tgacccgacc gggtgtccgt 1920
agttggcgcg gctaccttaa ccgcagggaa ttgtggaatt tatagttcta aattatatgt 1980
gggtggaacg gggaagctgg agcagatttt tggaggaaag caaaactggg gactttcagg 2040
actaggggcc tgggtctcag aagaatggga aaggacgaga aaggagtcta aataagaacc 2100
ctgctattag cattgtttgg ttttcttttc aggtgctgac ctgaacctgg ttcatccctt  2160
tctgaccaaa actgttcact caccgtggaa gggactaagc atccatatgg agacgccacc 2220
agtcaataca attggagaaa aggacacctc tcagccgcaa caagagtggg aaaagaacct 2280
t                                                                 2281
```

ASSAY METHODS FOR THE DETERMINATION OF FKBPL EXPRESSION LEVEL IN THE CONTEXT OF BREAST CANCER

FIELD OF INVENTION

The present invention relates to the use of FKBPL as a biomarker for making cancer treatment decisions and also as a predictive marker of cancer progression and disease free survival in relation to hormone responsive cancers, for example ovarian cancer, endometrial cancer, breast cancer and prostate cancer.

BACKGROUND OF THE INVENTION

Breast cancer is by far the most common cancer among women with around 1 million women worldwide being diagnosed with the disease each year. In the UK alone around 45,500 women are diagnosed with breast cancer annually.

Currently all breast cancer patients are assessed for oestrogen receptor (ER) and progesterone receptor (PR) status to determine the suitability of respective patients for endocrine or hormonal therapy. Endocrine or hormonal therapies are agents used to treat women with breast cancer who have hormone receptors on their breast cancer cells which allow the binding of hormone and include anti-oestrogens, for example tamoxifen and fulvestrant, and aromatase inhibitors which act to reduce the level of female hormones in the body.

Tamoxifen is typically provided to all oestrogen receptor positive (ER+) patients. However, only around 60% of these patients show a response to tamoxifen, with up to 40% of ER+ tumours failing to respond to or developing resistance to tamoxifen (non-responder subjects).

As tamoxifen is known to increase the risk of endometrial cancer, the provision of tamoxifen to subjects with non-responding tumours (non-responder subjects) needlessly increases the risk of these subjects to the risk of developing endometrial cancer.

Presently, a number of gene array panels are used to try and predict the probability of disease recurrence and determine the most suitable treatment for patients. One such gene panel is known as Oncotype DX. This gene panel cannot be used to select women for tamoxifen therapy. It only predicts recurrence in patients treated with tamoxifen and whether they would be likely to benefit from adjuvant chemotherapy. The assay requires formalin-fixed paraffin embedded (FFPE) tissue. A further panel known as the MammaPrint measures breast cancer recurrence independent of treatment. This panel requires fresh tissue composed of a minimum of 30% malignant cells.

Oncotype DX measures RNA levels of 21 genes (16 cancer genes and 5 reference genes) which demonstrate a consistent statistical link to distant breast cancer recurrence, as well as robust predictive power regarding chemotherapy benefit. MammaPrint measures RNA levels of 70 genes that are considered most informative regarding likelihood of tumour recurrence. Both these assays require expensive, sophisticated equipment.

Accurate prediction of a subject's response to endocrine therapy, would prevent potential non responders being treated with potentially harmful drugs when these may not provide a therapeutic benefit. In addition the determination of those cancer patients which would benefit from endocrine therapy, such as tamoxifen therapy, would allow targeting of such drug regimens and thus may provide for a reduction of healthcare budgets.

Furthermore, the ability to make predictions about cancer progression/disease free survival would enable the design of specific treatment strategies to prevent for example, metastasis following surgery and chemotherapy/endocrine therapy.

SUMMARY OF INVENTION

The present inventors have determined that FKBPL can provide an indication of patient response to endocrine therapies in addition to being a predictive marker of cancer progression and disease free survival.

FKBPL is an immunophilin-like protein that plays a role in the cellular stress response and includes three tetratricolpeptide repeat (TPR) motifs which are homologous to the Hsp90 interaction sites of other immunophilins that have roles in steroid hormone receptor signalling.

Accordingly, a first aspect of the present invention provides a method of characterising a cancer tissue, comprising:
determining in a test tissue sample an expression level of at least FKBPL, a variant of FKBPL, or a fragment of FKBPL or a variant of FKBPL, comparing the determined level with a control standard or the expression of FKBPL in a control sample;
wherein differential expression of FKBPL, in the test tissue sample, as compared to the control standard or the expression of FKBPL in a control sample, is indicative of the character of the cancer tissue.

Preferably, the gene encoding FKBPL (FK506 binding protein like) is FK506 protein like, as defined by Genbank Accession number AF139374, and Genbank Accession number AF139374.1 as disclosed by Robson et al. (1997) Gene regulation by low dose ionizing radiation in a normal human lung epithelial cell line, Biochem. Soc. Trans. 25(1), 335-342.

Optionally, the method may further comprise obtaining a biological sample from a subject.

FKBPL can be encoded by the nucleotide sequence Accession number NM_022110

(SEQ ID NO 1)
```
atggagacgc caccagtcaa tacaattggagaaaaggaca cctctcagcc gcaacaagag tgggaaaaga accttcggga gaaccttgattcagttattc agattaggca gcagcccga gaccctccta ccgaaacgct tgagctggaagtaagcccag atccagccag ccaaattcta gagcatactc aaggagctga aaaactggttgctgaacttg aaggagactc tcataagtct catggatcaa ccagtcagat gccagaggcccttcaagctt ctgatctctg gtactgcccc gatgggagct ttgtcaagaa gatcgtaatccgtggccatg gcttggacaa acccaaacta ggctcctgct gccgggtact ggctttggggtttcctttcg gatcagggcc gccagagggc
```

```
tggacagagc taactatggg cgtagggccatggagggagg aaacttgggg ggagctcata gagaaatgct tggagtccat gtgtcaaggtgaggaagcag agcttcagct gcctgggcac tctggacctc ctgtcaggct cacactggcatccttcactc aaggccgaga ctcctgggag ctggagacta gcgagaagga agccctggccagggaagaac gtgcaagggg cacagaacta tttcgagctg gaaccctga aggagctgcccgatgctatg gacgggctct cggctgctc ctgactttac ccccacctgg ccctccagaacgaactgtcc ttcatgccaa tctggctgcc tgtcagttgt tgctagggca gcctcagttggcagcccaga gctgtgaccg ggtgttggag cgggagcctg gccatttaaa ggccttataccgaaggggg ttgcccaggc tgcccttggg aacctggaaa aagcaactgc tgacctcaagaaggtgctgg cgatagatcc caaaaaccgg gcagcccagg aggaactggg gaaggtggtcattcaggga agaaccagga tgcagggctg gctcagggtc tgcgcaagat gtttggctgattaaaagtta aaccttaaaa gagaaaaaaa aaaaaaa,
``` and can have the amino acid sequence

```
                                          (SEQ ID NO 2)
METPPVNTIGEKDTSQPQQEWEKNLRENLDSVIQIRQQPRDPPT

ETLELEVSPDPASQILEHTQGAEKLVAELEGDSHKSHGSTSQMPEALQA

SDLWYCPDGSFVKKIVIRGHGLDKPKLGSCCRVLALGFPFGSGPPEGWT

ELTMGVGPWREETWGELIEKCLESMCQGEEAELQLPGHSGPPVRLTLA

SFTQGRDSWELETSEKEALAREERARGTELFRAGNPEGAARCYGRALR

LLLTLPPPGPPERTVLHANLAACQLLLGQPQLAAQSCDRVLEREPGHLK

ALYRRGVAQAALGNLEKATADLKKVLAIDPKNRAAQEELGKVVIQGKNQ

DAGLAQGLRKMFG
```
or be a variant or fragment thereof.

A FKBPL variant may be encoded by a nucleic acid sequence comprising

```
                                          (SEQ ID No 3)
atggagacgc caccagtcaa tacaattggagaaaaggaca cctctcagcc gcaacaagag tgggaaaaga accttcggga gaaccttgattcagttattc agattaggca gcagccccga gaccctccta ccgaaacgct tgagctggaagtaagcccag atccagccag ccaaattcta gagcatactc aaggagctga aaaactggttgctgaacttg aaggagactc tcataagtct catggatcaa ccagtcagat gccagaggcccttcaagctt ctgatctctg gtactgcccc gatgggagct ttgtcaagaa gatcgtaatccgtggccatg gcttggacaa acccaaacta ggctcctgct gccgggtact ggctttggggtttcctttcg gatcagggcc gccagagggc tggacagagc taactatggg cgtagggccatggagggagg aaacttgggg ggagctcata gagaaatgct tggagtccat gtgtcaaggtgaggaagcag agcttcagct gcctgggcac actggacctc ctgtcgggct cacactggcatccttcactc aaggccgaga ctcctgggag ctggagacta gcgagaagga agccctggccagggaagaac gtgcaagggg cacagaacta tttcgagctg gaaccctga aggagctgcccgatgctatg gacgggctct cggctgctc ctgactttac ccccacctgg ccctccagaacgaactgtcc ttcatgccaa tctggctgcc tgtcagttgt tgctagggca gcctcagttggcagcccaga gctgtgaccg ggtgttggag cgggagcctg gccatttaaa ggccttataccgaaggggg ttgcccaggc tgcccttggg aacctggaaa aagcaactgc tgacctcaagaaggtgctgg cgatagatcc caaaaaccgg gcagcccagg aggaactggg gaaggtggtcattcaggga agaaccagga tgcagggctg gctcagggtc tgcgcaagat gtttggctgattaaaagtta aaccttaaaa gagaaaaaaa aaaaaaa
``` and have the amino acid sequence

```
                                              (SEQ ID No 4)
METPPVNTIGEKDTSQPQQEWEKNLRENLDSVIQIRQQPRDPPTETLEL

EVSPDPASQILEHTQGAEKLVAELEGDSHKSHGSTSQMPEALQASDLW

YCPDGSFVKKIVIRGHGLDKPKLGSCCRVLALGFPFGSGPPEGWTELTM

GVGPWREETWGELIEKCLESMCQGEEAELQLPGHTGPPVGLTLASFTQ

GRDSWELETSEKEALAREERARGTELFRAGNPEGAARCYGRALRLLLTL

PPPGPPERTVLHANLAACQLLLGQPQLAAQSCDRVLEREPGHLKALYRR

GVAQAALGNLEKATADLKKVLAIDPKNRAAQEELGKVVIQGKNQDAGLA

QGLRKMFG.
```

In particular, the present inventors have determined that oestrogen receptor positive (ER+) tumour cells or cancers which stably express FKBPL have the character that they are highly sensitive to anti-oestrogen agents, for example tamoxifen and fulvestrant. In support of this work, the inventors have determined that siRNA knock-down of FKBPL dramatically increased the resistance of ER+ cells to tamoxifen and suggests that FKBPL level could predict cancer progression and disease free survival.

By differential expression it is meant that following detection of FKBPL in the test tissue sample and the control sample, the level of FKBPL in a sample can be scored for example 0 (no detectable FKBPL), 1 (low detectable level of FKBPL), 2 (medium detectable level of FKBPL), 3 (High detectable level of FKBPL) and then the level detected between the test sample and the control sample compared. Detection may be by, for example, staining following suitable immunohistochemistry for FKBPL. Alternatively, detection may allow quantitative measurement of FKBPL in a test sample and a control sample. In embodiments, FKBPL levels could be assessed before treatment with any agent and the levels of FKBPL at that point scored as either 0, 1, 2, 3. These values could then be used to predict response to either ER modulating drugs, chemotherapy/radiation or new drugs. In embodiments it would not be required to re-evaluate FKBPL levels after each treatment to determine whether a patient would respond.

By highly sensitive is meant a tumour cell which is greater than 80%, more preferably greater than 85%, more preferably greater than 90%, more preferably greater than 95%, even more preferably greater than 99% more likely to be inhibited from proliferating (responsive to treatment) following treatment of the tumour cell with a hormonal or anti-oestrogen agent than a tumour cell which expresses reduced levels of FKBPL. With respect to cancer, cancer which is highly sensitive is meant a cancer is greater than 80%, preferably greater than 85% preferably greater than 90%, more preferably greater than 98% and even more preferably greater that 99% more likely to be inhibited following treatment of the cancer subject than a cancer subject with a cancer which exhibits reduced levels of FKBPL. Cancer is inhibited if at least one symptom of the cancer is alleviated, terminated, slowed down or prevented. As used herein, cancer is also inhibited if recurrence or metastasis of the cancer is reduced, slowed, delayed or prevented.

In embodiments of the invention, anti-oestrogen agents can be selected from selective oestrogen receptor modulators, selective oestrogen receptor downregulators or aromatase inhibitors. Examples of such inhibitors are provided at Table 1. ER+ cells will typically respond to tamoxifen, but the presence of increased FKBPL levels in comparison to a control in combination with ER+ causes a dramatic additional increase in the sensitivity of the tumour cell or cancer to such endocrine drugs. Examples of endocrine drugs which can be provided in table 1.

TABLE 1

| Class of Drug | Mechanism of Action | Examples of Drug Types (Commercial Name) |
|---|---|---|
| Selective Estrogen Receptor Modulator (SERM) | Binds ER to prevent oestrogen binding its receptor thereby inhibiting ER signalling | Tamoxifen (Nolvadex) Raloxifene (Evista) Toremifene (Fareston) |
| Selective Estrogen Receptor Downregulator (SERD). | Binds ER to prevent oestrogen binding its receptor thereby inhibiting ER signalling. Degrades ER | Fulvestrant (Faslodex) |
| Aromatase Inhibitors | Inhibits synthesis of oestrogen by blocking action of aromatase enzyme which normally converts androgen to oestrogen | Anastrozole (Arimidex) Exemestane (Aromasin) Letrozole (Femara) |

In embodiments, the cancer tissue may be characterised by considering the expression level of FKBPL in combination with the expression level of at least one additional biomarker, for example oestrogen receptor. In embodiments of the method, FKBPL, as a predictor of anti-oestrogen response, in particular tamoxifen response or cancer progression/disease free survival can be used along with other standard biomarkers. The markers may be selected such that the positive predictive value of the methods of the invention are at least about 10%, preferably about 25% more preferably about 50% and most preferably 90%. Accordingly, in embodiments of the method there is provided a method of determining the level of expression of FKBPL in a tumour sample and determination of a level of expression of at least one of oestrogen receptor (ER) and progesterone receptor (PR).

Suitable biomarkers for use in addition to FKBPL are; breast-associated mucin CA15-3, CA 27.29, oestrogen receptor α and β, progesterone receptor, Human Epidermal growth factor Receptor 2 (HER2), urokinase Plasminogen Activator (uPA) and Plasminogen Activator Inhibitor-1 (PAI-1), cathepsin D, cyclin dependent kinase inhibitor (p21), S118ER, S167ER, ADAM metallopeptidase domain 9 (ADAM9), BCL-2, MYC, TP53, BAG-1, HOXB13, IL17BR, the ER coactivators, SRC-1 and SRC-3 (AIB1) or the ER corepressor, NCoR1, AKT and pAKT or XAP3. Furthermore, FKBPL could be used in combination with some or all of the markers in the Oncotype Dx or MammaPrint arrays. In embodiments 50 markers or less can be used in combination with FKBPL. In alternative embodiments, 20 markers or less can be used in combination with FKBPL, in further embodiments 10 markers or less, or 5 markers or less can be used in combination with FKBPL.

Measuring FKBPL expression levels in combination with the p21 and/or cathepsin D may be advantageous to increase the specificity of any diagnostic or prognostic test of the invention.

The inventors have determined that FKBPL increases the phosphorylation of ER. Phosphorylation status of ER could be used in combination with the determination of the expression level of FKBPL to increase the specificity of a test of the invention.

In embodiments of the invention when the method is as an indicator for disease free survival and to provide a basis for treatment decisions, the cancer tissue can be cancer tissue from subjects with a hormone responsive cancer, for example ovarian, endometrial, prostate or breast cancer. In preferred embodiments the cancer tissue can be breast cancer tissue.

In embodiments of the invention, characterising a cancer tissue can comprise determining a prognosis of a subject with the cancer wherein a reduced expression of FKBPL, for example a reduced mRNA level of FKBPL, predicts for a worse outcome and prognosis.

In another embodiment of the invention, the method of characterising the cancer tissue sample can include a step of predicting the ability of an agent to inhibit or decrease the progression of the cancer. For example a cancer tissue could be tested to determine whether an agent which selectively modulates an oestrogen receptor present in a cancer tissue or lowers the circulating levels of oestrogen in a cancer tissue, is able to inhibit the cancer in a subject from which the cancer tissue being tested.

In embodiments of the invention determining the expression level of FKBPL comprises measuring the level of an expression product of the FKBPL encoding gene. In embodiments of the invention determining the expression of level of an expression product can include determining the activity and/or the location of FKBPL. Determination of the activity of FKBPL may be performed by any means known in the art. Determining the location of FKBPL may be performed using any means known in the art, for example tagging FKBPL with a detectable marker and analoging the cell. As will be understood in the art, gene expression, for example of FKBPL, is a multistep process in which genetic information of a cell encoded in the genome is transcribed to produce RNA, for example mRNA and the mRNA transcript is translated to produce corresponding protein. An increased or decreased level of FKBPL can be detected by an increase or decrease in any expression product, for example mRNA or protein. The expression product, such as mRNA or a protein, may be suitably determined using, for example, an antibody or binding fragment thereof with binding specificity to FKBPL. In embodiments the level of expression of protein product can be determined using an immunohistochemical (IHC) or ELISA based assay. Alternatively mRNA levels of FKBPL can be detected using microarray analysis or Real-time PCR. A simple IHC or ELISA test for FKBPL requiring only formalin fixed paraffin-embedded (FFPE) tissue would be advantageous as it could be used on its own or in combination with an ER/PR test, making it inexpensive, and easy to integrate into the current NHS screening system. An embodiment of the invention can be an IHC or ELISA test for FKBPL alone to test biological samples or tissue samples.

As FKBPL is a secreted protein, it may therefore be detected in biological fluids.

An increase or decrease in an expression product, for example an mRNA transcript or an FKBPL protein may be at least about 1%, at least about 2%, at least about 5%, at least about 10%, at least about 20%, at least about 25%, at least about 30%, at least about 50%, at least about 75%, at least about 100% or more, higher or lower than a control. Alternatively, the expression product may be increased or decreased at least about 2 fold, at least about 3 fold, at least about 5 fold, at least about 8 fold, at least about 10 fold, at least about 20 fold, at least about 100 fold from the control. In embodiments where protein expression is determined by immunohistochemistry, the expression product may be measured semi-quantitatively, for example with protein expression levels being noted 0, 1, 2 and 3 with 0 being no detectable increase in expression from control and 3 being the highest detected protein expression.

In embodiments, when FKBPL is detected in a tumour cell at an increased level relative to a control, the tumour cell can be more sensitive to an agent which selectively modulates an oestrogen receptor present in a cancer tissue or lowers the circulating levels of oestrogen in a cancer tissue, for example hormonal treatments including tamoxifen, fulvestrant and aromatase inhibitors. In embodiments, when FKBPL is detected in a tumour cell at an increased level relative to a control, this can be indicative of disease free survival of a subject.

In other embodiments, FKBPL localisation i.e. within the cytoplasm rather than the nucleus or vice versa may also affect response to endocrine therapies and therefore effect disease free survival. The methods of the invention may be used in predictive medicine, to provide a diagnostic assay, prognostic assay, or a predicitive assay to monitor neoplastic disease, in particular hormone responsive cancer, such as, but not limited to ovarian cancer, endometrial cancer, breast cancer and prostate cancer.

Typically in such methods a biological sample can be a blood sample, a serum sample, or cells or tissue isolated from a subject using standard procedures, for example a needle biopsy. Early diagnosis allows the provision of suitable therapy to a subject and may thus enhance the success of a therapy. A cancer cell, including a tumour cell refers to a cell that divide at an abnormal (increased) rate.

Further, the assay may allow determination of the likely success of a therapy, for example as a prognostic assay to determine the positive or negative likelihood of disease free survival, following medical intervention or lack of intervention. For example the method may be provided to determine the most effective treatment or combination of treatments, for example small molecules, agonists, antagonists, proteins and peptides, antibodies and antibody fragments, peptidomimetics, nucleic acids, radiotherapy, chemotherapy and the like.

According to a second aspect of the present invention there is provided a kit for predicting the sensitivity of a tumour cell to an agent which selectively modulates an oestrogen receptor present in a cancer tissue or lowers the circulating levels of oestrogen in a cancer tissue, (for example an agent may be tamoxifen, fulvestrant or an aromatase inhibitor), the kit comprising means for detecting in a biological sample FKBPL expression, or expression of an FKBPL variant, or expression of a transcript or protein of a fragment thereof.

In embodiments, the kit can be suitable for indicating disease for survival of a subject.

A kit is any manufacture (for example a package or container) comprising at least one reagent, for example a probe, for example primers, or antibodies, specifically for detecting FKBPL. The manufacture may be promoted, distributed, or sold as units for performing the present invention. Such kits can be conveniently used in clinical settings.

Tumour cells with an increased sensitivity to an agent which selectively modulates an oestrogen receptor present in a cancer tissue or lowers the circulating levels of oestrogen in a cancer tissue reduces the ability of the cancer to progress, for example the tumour cell to proliferate.

In embodiments of the invention, the means for detecting in a biological sample can be an antibody with binding specificity for FKBPL or a fragment thereof. In alternative embodiments, the means for detecting in a biological sample can be a nucleic acid probe with binding specificity for FKBPL. In embodiments, a nucleic acid probe may be specific for a FKBPL gene, a FKBPL mRNA transcript, or may be a pair of primers for amplification of a FKBPL gene or a portion thereof.

In specific embodiments, FKBPL protein can be detected using a first antibody with binding specificity to FKBPL. In such embodiments, a second antibody with binding specificity to the first antibody can be provided wherein the second antibody can be conjugated to a detectable label, for example, an enzyme such as horseradish peroxidase, alkaline phosphatase, and other enzymes commonly known in the art, a fluorescent label or fluorophore, chromophore or a radioactive label. The term antibody refers to an immunoglobulin molecule or combinations thereof that specifically binds to or is immunologically reactive with a particular antigen and includes polyclonal, monoclonal, genetically engineered and otherwise modified forms of antibodies, not limited to chimeric antibodies, humanised antibodies, heteroconjugate antibodies (for example bispecific antibodies, diabodies, triabodies, and tetrabodies), single chain Fv antibodies (scFv), or polypeptides that contain at least a portion of immunoglobulin that is sufficient to confer specific antigen binding to the polypeptide. Antibody fragments include proteolytic antibody fragments such as F(ab')2 fragments, Fab' fragments, Fab'-SH fragments, Fab fragments, FV, rIgG, recombinant antibody fragments such as sFv fragments, dsFv fragments, bispecific sFv fragments, bispecific dsFv fragments, complementarity determining region (CDR) fragments, camelid antibodies and antibodies produced by cartilaginous and bony fishes and isolated binding domains thereof. A Fab fragment is a monovalent fragment consisting of the VL, VH, CL and CH1 domains; a F(ab')2 fragment is a bivalent fragment comprising two Fab fragments linked by a disulphide bridge at the hinge region, an Fd fragment consists of the VH and CH1 domains; an FV fragment consists of the VL and VH domains of a single arm of an antibody; and a dAb fragment consists of a VH domain. A single chain antibody (scFv) is an antibody in which a VL and VH region are paired to form a monovalent molecule via a synthetic linker that enables them to be made as a single protein chain. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites. A chimeric antibody is an antibody that contains one or more regions from one antibody and one or more regions from one or more other antibodies. An antibody may have one or more binding sites. If there is more than one binding site, the binding sites may be identical to one another or may be different. For instance, a naturally occurring immunoglobulin has two identical binding sites, a single chain antibody or Fab fragment has one binding site, while a bispecific or bifunctional antibody has two different binding sites.

In embodiments, the kit can include a control sample, such as a cell line or tissue sample known not to express FKBPL or to express FKBPL at a certain level, in particular breast cancer cell lines or tissues for which the expression level of FKBPL has been previously determined. In embodiments, a suitable control cell line can be MCF7 or T47D where the expression level of FKBPL is known.

In some embodiments, a kit includes instructional material disclosing, for example, means of use of a probe or an antibody that specifically binds an FKBPL expression product, for example mRNA transcript or protein. The instructional materials can be in written or provided in an electronic form.

In a specific embodiment, an antibody provided in the kit or used in the methods of the invention can be FKBPL rabbit polyclonal primary antibody (ProteinTech, IL, USA, Cat no. 10060-1-AP) (primary antibody). In such an embodiment anti-rabbit IgG HRP-linked whole antibody secondary (GE Healthcare, Cat no. NA934V), can be used to detect the primary antibody.

According to a third aspect of the present invention, there is provided a method of treating a subject with cancer comprising the steps:

determining in a test sample an expression level of at least FKBPL, a variant of FKBPL or a fragment of FKBPL or an FKBPL variant, comparing this expression level of FKBPL, a variant of FKBPL or a fragment of FKBPL or FKBPL variant to that determined in a control standard or the expression of FKBPL, a variant of FKBPL or a fragment of FKBPL or FKBPL variant in a control sample, wherein, when the expression level of FKBPL in the test sample is increased relative to the control standard or the expression of FKBPL in a control sample, the subject is provided with an agent which selectively reduces the level of oestrogen receptor present in a cancer tissue or lowers the circulating levels of oestrogen in a cancer tissue of the subject.

According to a fourth aspect of the present invention there is provided a method of monitoring the treatment of a subject with cancer, comprising the steps:

determining in a test sample an expression level of at least FKBPL, or a variant thereof, or a fragment of FKBPL or variant of FKBPL.

comparing the detected level to the expression of FKBPL in a control cancer sample;

wherein when the expression level of FKBPL is decreased in the test sample relative to the control sample, it is indicative that the cancer is less sensitive to an agent which selectively modulates oestrogen receptor present in the cancer tissues or lowers the circulating levels of oestrogen in the cancer tissue than in the control sample.

In embodiments of a method of the invention the control sample can be obtained from a subject prior to the onset of cancer. In alternative embodiments the control sample can be obtained from a subject prior to the start of a treatment regimen for the cancer. In a further embodiment, the control sample can be provided at a first period in time prior to the provision of the test sample at a second period of time. The difference between the first period of time and the second period of time can be 1 day, 2, 3, 4, 5 or 6 days, 1 week, or 2, 3, 4 weeks, at least 1 month, 2, 3, 4, 5 or at least 6 months. Suitably a cancer treatment regimen can be a first, second, third or more cancer treatment regimen provided to a subject.

When the level of FKBPL is increased in the test sample from the level detected in a control sample, it is indicative that the tumour is more sensitive to anti-oestrogen therapy, for example a selective estrogen receptor modulator (tamoxifen), a selective estrogen receptor downregulator (fulvestrant), or an aromatase inhibitor, at the second period of time and thus provision of such a therapy to a subject may increase disease free survival.

When the level of FKBPL is decreased in the test example from the level detected in the control sample, it is indicative that the tumour is less sensitive to anti-oestrogen therapy and there is a greater likelihood of disease progression.

In embodiments of the invention, diagnosis, monitoring or prognostication a cancerous or malignant condition in a subject can be provided by:
(i) providing a test sample from the subject,
(ii) determining in the sample an expression level of at least one of FKBPL, a variant of FKBPL, a fragment of FKBPL or an FKBPL variant,
(iii) comparing the determined level to the expression of FKBPL in the test sample to that in a control sample;
wherein when the expression level of FKBPL is decreased in the test sample relative to the control sample, it is indicative that the cancer is less sensitive to an agent which selectively modulates oestrogen receptor present in the cancer tissue or lowers the circulating levels of oestrogen in the cancer tissue.

In an another embodiment, the invention provides for optimizing an existing therapeutic agent against cancer, the invention comprising the steps:
(i) providing a first test sample from a subject with cancer,
(ii) providing a second test sample from the subject with cancer after administration of a therapeutic agent to the subject,
(iii) determining the expression level of FKBPL or a variant of FKBPL, or a fragment thereof in the first and second samples, and
(iv) comparing the expression level of FKBPL or a variant of FKBPL or a fragment thereof in the first and second samples wherein when the level of FKBPL is increased it is indicative the subject will have an increased likelihood of disease survival.

Optimisation may be to determine the optimal therapeutic agent to use or to determine the concentrations or treatment regimens which should be used.

In yet another embodiment there is provided a method of testing a therapy or a new therapeutic agent for treating cancer the method comprising:
(i) providing a first sample,
(ii) providing a second sample wherein the second sample has been exposed to a new therapy or therapeutic agent,
(iii) determining the expression level of FKBPL or a variant of FKBPL or a fragment thereof in the first and second samples, and
(iv) comparing the expression level of FKBPL or a variant of FKBPL or a fragment thereof in the first and second samples, wherein
when the level of FKBPL is increased, this is indicative that the new therapy or therapeutic agent will increase the likelihood of disease free survival of a subject with cancer if provided with the new therapy or therapeutic agent.

As will be appreciated, the methods of the present invention can be applied to cancer including, for example, breast cancer, ovarian cancer, endometrial cancer and prostate cancer.

Biological samples for use in the present invention may include tissue samples (such as breast tissue biopsies, or breast cancer cell samples) or biological fluids. Suitably a sample may be a body fluid or body tissue from a subject with cancer. The sample may be for example, whole serum, blood plasma, urine, seminal fluid, or seminal plasma. The particular type of body fluid or body tissue depends on the type of cancer and the subject. In some embodiments, samples of body fluid or tissue can be obtained from tumour cells. Samples may be fresh or processed, for example fixed. In particular embodiments, a sample may be provided to a solid support, for example a microscope slide, a tissue culture dish, a multi-well plate or membrane, BIACORE™ or protein or nucleic acid chip. Typically the sample can be formalin fixed paraffin embedded tissue or freshly frozen tissue or blood, or a sample provided using any other methods for tumour preservation and storage.

The sample may be suitably obtained from the subject before or after administration of a therapeutic agent. As will be appreciated, if a method to treat or optimise treatment of a subject's cancer is being used, the preferred sample is a sample of the subject's cancer. Alternatively, a cancer cell line similar to the type of cancer being treated can be assayed. If the method is being used to identify a new therapy or therapeutic agent, any appropriate cell line may be used.

Determining Gene Expression Level

Gene expression levels may be determined using any technique known in the art, for example methods based on hybridisation of polynucleotides (mRNA transcripts), methods based on sequencing polynucleotides or amplifying polynucleotides.

Quantification of mRNA gene transcript in a sample may be performed using, without limitation, northern blotting, in situ hybridisation, RNAse protease assays, PCR based methods such as reverse transcription polymerase chain reaction (RT-PCR) and real time quantitative PCT qRT-PCR. Alternatively, antibodies with binding specificity to nucleic acid duplexes may be used to determine mRNA levels. Microarray techniques using specific binding members for RNAs of interest, for example cDNA or oligonucleotide probes specific for RNAs of interest or antibodies specific for mRNA of interest wherein the specific binding members are plated or arrayed on a substrate, for example a glass slide or a microchip substrate can be used. The specific binding members may be provided on the substrate at an addressable location and the number of addressable locations can vary from, for example at least three, at least 10, at least 50, at least 100, at least 1000 or at least 10,000 or more. In embodiments the number of addressable locations can vary from less than 1000, less than 100, less than 50, less than 10, or less than 5. In such embodiments the sample is contacted with the array and the arrayed specific binding members can form detectable interactions with targets in the sample. The interactions may be detected using suitable labels. Where oligonucleotide probes are utilised, under appropriate conditions the oligonucleotide probes can "hybridise" to a target nucleic acid sequence to form base-paired duplexes with nucleic acid molecules that have a complementary base sequence. Hybridisation conditions resulting in particular degrees of stringency will vary depending on the nature of the hybridisation method and the composition and length of the hybridising nucleic acid sequences.

Stringent hybridisation occurs when a nucleic acid binds a target nucleic acid with minimal background. Typically, to achieve stringent hybridisation, temperatures of around 1° C. to about 20° C., more preferably 5° C. to about 20° C. below the Tm (melting temperature at which half the molecules dissociate from their partner) are used. However, it is further defined by ionic strength and pH of the solution. Suitable hybridisation conditions would be known to those of skill in the art, and exemplary hybridisation conditions are:

Very high stringency (detects sequences that share at least 90% identity)—hybridisation 5×SSC at 65° C. for about 16 hours, High stringency (detects sequences that share at least 80% identity)—hybridisation 5×-6×SSC at 65° C. for 16 hours, and Low stringency (detects sequences that share at least 50% identity)—hybridisation 6×SSC at room temperature to 55° C. for 20 to 30 minutes.

An example of a highly stringent wash condition is 0.15 M NaCl at 72° C. for about 15 minutes. An example of a stringent wash condition is 0.2× sodium chloride and sodium citrate (SSC) wash at 65° C. for 15 minutes (see, Sambrook and Russell, infra, for a description of SSC buffer for example 20×SSC made by dissolving 175.3 g of NaCl and 88.9 g of sodium citrate in 800 ml distilled water. Adjusting pH to pH7.0 with HCl (IM) and adjusting volume to IL with distilled water). Often, a high stringency wash is preceded by a low stringency wash to remove background probe signal. An example of a medium stringency wash for a duplex of, for example, more than 100 nucleotides, is 1×SSC at 45° C. for 15 minutes. An example of a low stringency wash for a duplex of, for example more than 100 nucleotides, is 4-6×SSC at 40° C. for 15 minutes. For short probes (for example about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (for example, >50 nucleotides).

The methodology used in PCR methods for example RT-PCR and PCT and RT-PCR will be well known to those skilled in the art.

Some methods may require the isolation of RNA from a sample. Such isolation techniques are known in the art and may utilise commercially available RNA isolation kits from manufacturers such as Qiagen.

Determination of Protein Expression

Immunohistochemistry (IHC) and ELISA are techniques useful for detecting protein expression. Antibodies or binding fragments of antibodies (monoclonal or polyclonal) may be used in the disclosed methods and kits. Antibodies can be detected by direct labelling of the antibodies or by using a second antibody which is specific for the primary antibody which has binding specificity for the target. The second antibody can be labelled with a detectable moiety or can be conjugated to a hapten (such as a biotin or the like) wherein the hapten is detectable by a detectably labelled cognate hapten binding molecule, for example streptavidin horseradish peroxidise.

The binding specificity of FKBPL antibodies (antibodies with binding specificity to FKBPL) can be established using Western blotting, in parallel with immunohistochemical analysis of formalin-fixed, paraffin-embedded cell lines mimicking the handling of the primary tumours (as described by O'Brien et al., 2007, International Journal of Cancer, 120: 1434-1443). In brief, a parental MCF-7 breast cancer cell line +/−FKBPL targeted siRNA, together with FKBPL overexpressing stable clones may be used to optimize anti-FKBPL antibodies. Cell lines may be fixed in PFA for 30 min and resuspended in 70% ethanol overnight before being embedded in paraffin and arrayed using a tissue arrayer. Immunocytochemically stained cell pellet arrays may then be compared with Western blot data to check the specificity and suitability of the antibodies and the significance of correlations determined using Spearman's rank test. The antibody displaying the most comparable expression levels between the two assays may be used for screening.

Alternatively, proteins may be detected using aptamers (for example a single stranded nucleic acid molecule (such as, DNA or RNA) that assumes a specific, sequence dependent shape and binds to FKBPL protein with high affinity and specificity), mirror image aptamers (SPIEGELMER™), engineered nonimmunuoglobulin binding proteins, for example nonimmunoglobulin binding proteins based on scaffolds including fibronectin (ADNECTINS™), CTLA-1 (EVIBODIES™), lipocalins (ANTICALINS™), protein A domain (AFFIBODIES™) or the like. In embodiments, an aptamer may comprise less than 100 nucleotides, less than 75 nucleotides, less than 50 nucleotides, for example 25 to 50 nucleotides, 10 to 50 nucleotides, 10 to 100 nucleotides.

In particular embodiments, an array may be provided comprising protein sequences, including FKBPL or fragments of FKBPL or antibodies with binding specificity to FKBPL or fragments thereof. These protein sequences or antibodies can be conjoined to a substrate. Changes in protein expression can be detected by, for example, measuring the level of FKBPL in a sample which binds to antibodies with binding specificity to FKBPL when the sample to be tested is brought into contact with the array.

Suitable substrates for use in an array and array formats would be known to those of skill in the art.

In particular embodiments IHC samples can be analysed using an automated image analysis system, so as to provide a blinded analysis. For this, whole-slide digital images can be first captured at 20× using a ScanScope XT Slide Scanner (Aperio Technologies). Secondly, a positive pixel count algorithm (Aperio Technologies) can be used to develop a quantitative scoring model for FKBPL expression. Statistical analysis of tissue microarray-derived data can be carried out using the v2 test for trend, Fisher's exact and Mann-Whitney tests for comparison of FKBPL expression between tamoxifen responding and non-responding tumours and Kaplan-Meier plots can be used for survival analysis and the curves compared using the log-rank test. Cox proportional hazards regression can be used to estimate proportional hazard ratios and conduct multivariate analyses as described previously. All calculations can be performed with SPSS v11.0 (SPSS, IL). In addition, to facilitate generation of discrete multi-marker test, fluorescently-tagged antibodies (carrying non-overlapping fluorophores) against FKBPL, ER and PR (in the first instance) then additional relevant biomarkers can be used simultaneously. Advantageously a recently developed fluorescent scanning system from Aperio, for example, the ScanScope FL system could be used. This assay method would provide a further layer of sophistication by providing more quantitative analysis than that afforded by conventional brightfield imaging.

As will be appreciated, the methods of detecting the expression of FKBPL, the location of FKBPL in a cell or the activity of FKBPL may be applicable in relation to any of the methods of the invention described herein or claimed.

Preferred features and embodiments of each aspect of the invention are as for each of the other aspects mutatis mutandis unless context demands otherwise.

DEFINITIONS

Cancer is a malignant neoplasm, for example one that has undergone characteristic anaplasia with loss of differentiation, increased rate of growth, invasion of surrounding tissue and is capable of metastasis.

A nucleic acid molecule is said to be complementary with another nucleic acid molecule if the two molecules share a significant number of complementary nucleotides to form a stable duplex or triplex when the strands bind (hybridise) to each other, for example by forming Watson-Crick base pairs. Complementarity can be described as a percentage of the proportion of base pairs between two nucleic acid molecules within a specific region of two molecules.

By contact is meant to bring an agent into close proximity with another agent such that both agents can interact with each other. For example an antibody or other binding member may be brought into close proximity with a protein in a sample and where the antibody has binding specificity for the protein the antibody will bind the protein. Alternatively, a first nucleic acid may be brought into close proximity with a second complementary nucleic acid (a primer with a target sequence) and can be incubated such that binding may be detected or amplification of the target sequence may occur.

By detect is meant determining if an interaction between two agents for example two proteins or two nucleic acids is present or absent. This may include quantification. Detection may include the use of an agent which is capable of detection (a label) using for example spectrophotometry, flow cytometry, or microscopy. Exemplary labels include radioactive isotopes (such as $^3H$, $^{14}C$, $^{15}N$, $^{35}S$, $^{90}V$, $^{99}Tc$, $^{111}Ln$, $^{125}I$, or $^{131}I$) fluorophores (such as fluorescein, fluorescein isothiocyanate, rhodamine or the like), chromophores, ligands, chemiluminescent agents, bioluminescent agents (such as luciferase, green fluorescent protein (GFP) or yellow fluorescent protein), enzymes that can produce a detectable reaction product (such as horseradish peroxidise, luciferase, alkaline phosphatase, beta-galactosidase) and combinations thereof.

By specific binding is meant a particular interaction between one binding partner and another binding partner, for example a primer and a target sequence or a protein specific antibody and a protein. Interactions between one binding partner and another binding partner may be mediated by one or more, typically more than one, non-covalent bonds. An exemplary way of characterising specific binding is by a specific binding curve.

Unless otherwise explained, all technical and scientific terms used herein have the same meaning as commonly understood by one of ordinary skill in the art to which a disclosed invention belongs. The singular terms "a", "an", and "the" include plural references unless the context clearly indicates otherwise.

As used herein a "subject" may be an animal, in particular a mammal. For example, the subject may be a human. In alternative embodiments, the subject can be male or female. In certain embodiments, the subject can be a patient under medical care, or actively seeking medical care for cancer.

An FKBPL variant may be a protein of SEQ ID No 2 wherein 25 or fewer, more preferably 15 or fewer, even more preferably of 10 or fewer, 2 or fewer amino acids are inserted, deleted or substituted, whilst providing a protein with FKBPL activity.

A fragment of FKBPL or an FKBPL variant may comprise a stretch of amino acid residues of at least 5 to 7 contiguous amino acids, often at least 7 to 9 contiguous amino acids, typically 9 to 13 contiguous amino acids, more preferably at least 20 to 30 or more contiguous amino acids, most preferably at least 30 to 40 or more consecutive amino acids.

Throughout the specification, unless the context demands otherwise, the terms 'comprise' or 'include', or variations such as 'comprises' or 'comprising', 'includes' or 'including' will be understood to imply the method or kit includes a stated integer or group of integers, but not the exclusion of any other integer or group of integers.

Each document, reference, patent application or patent cited in this text is expressly incorporated herein in their entirety by reference, which means it should be read and considered by the reader as part of this text. That the document, reference, patent application or patent cited in the text is not repeated in this text is merely for reasons of conciseness. Reference to cited material or information contained in the text should not be understood as a concession that the material or information was part of the common general knowledge or was known in any country.

Embodiments of the present invention are now described with reference to the following figures in which FIG. 1 shows positive interaction exists between Hsp90, FKBPL and oestrogen receptor in MCF-7 cells (using co-immunoprecipitation) and that FKBPL co localises with tubulin;

FIG. 2 illustrates FKBPL interaction with the ubiquitin-related proteins, XAP3 and USP19 in yeast cells;

FIG. 4 shows FKBPL overexpression inhibits the clonogenic potential of ER+ve MCF-7 cells following oestrogen deprivation and slows growth of breast cancer cells;

Figure 5A:
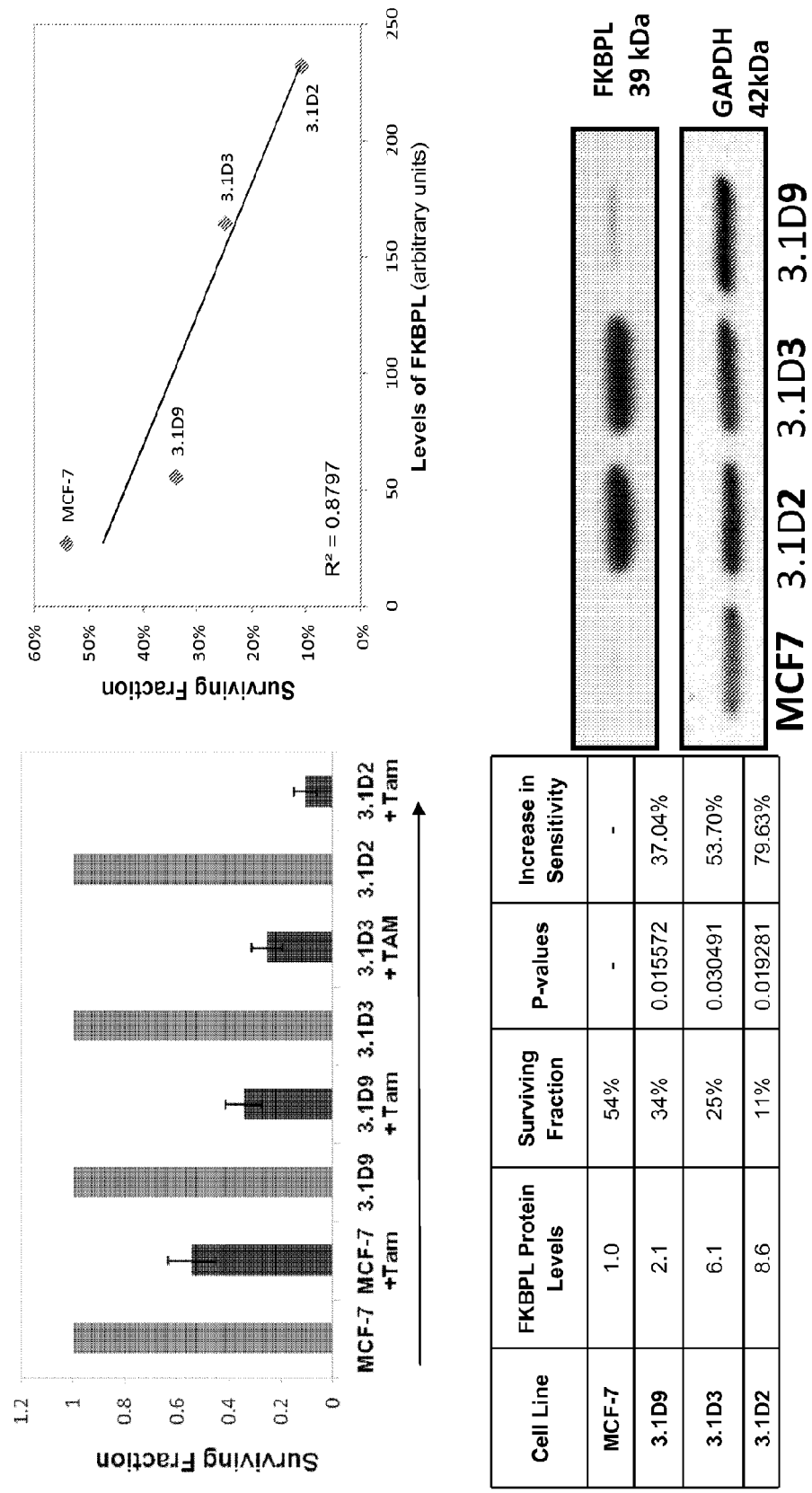
Figure 5B:
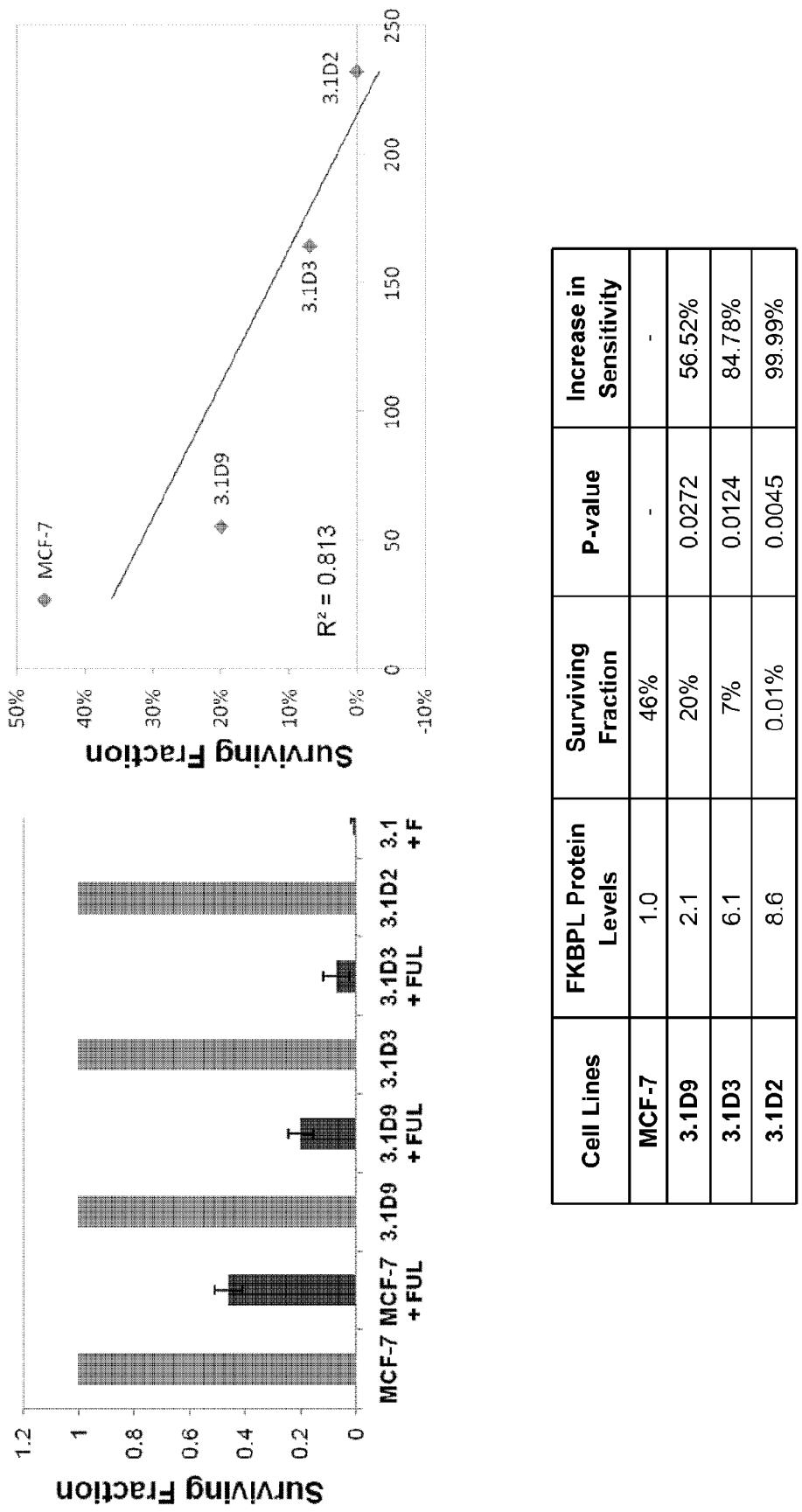
Figure 5C:
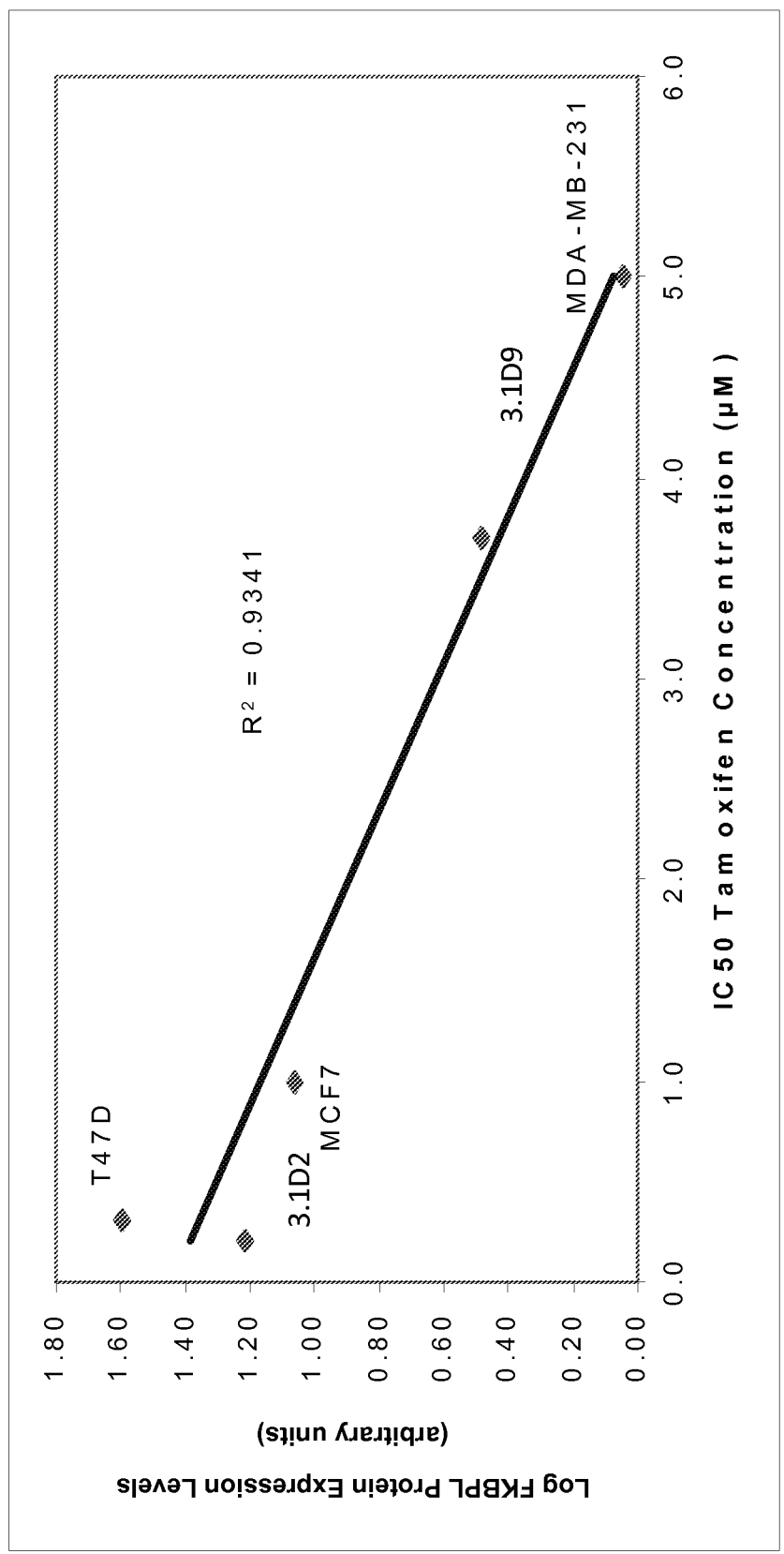
Figure 5D:
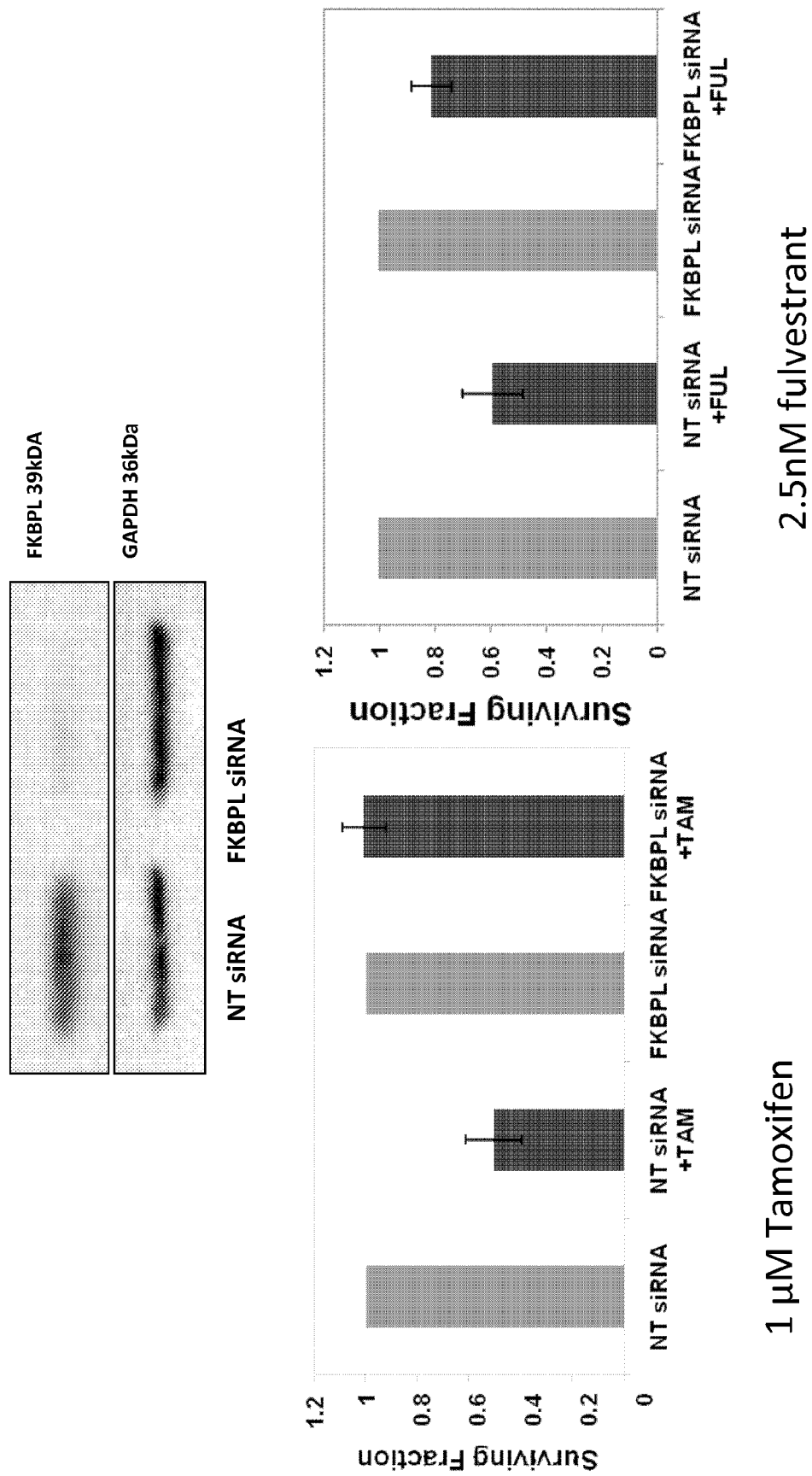
Figure 7A:
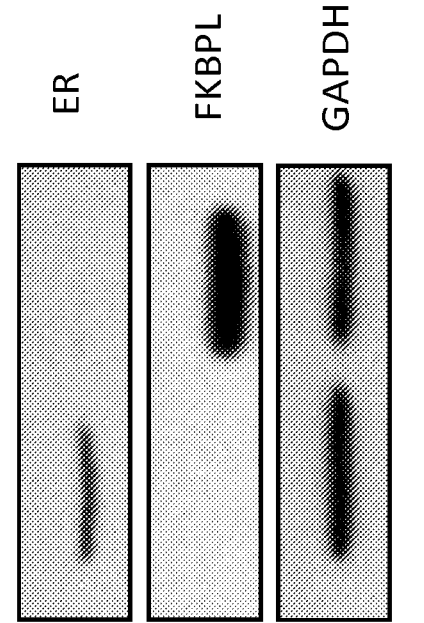
Figure 7B:
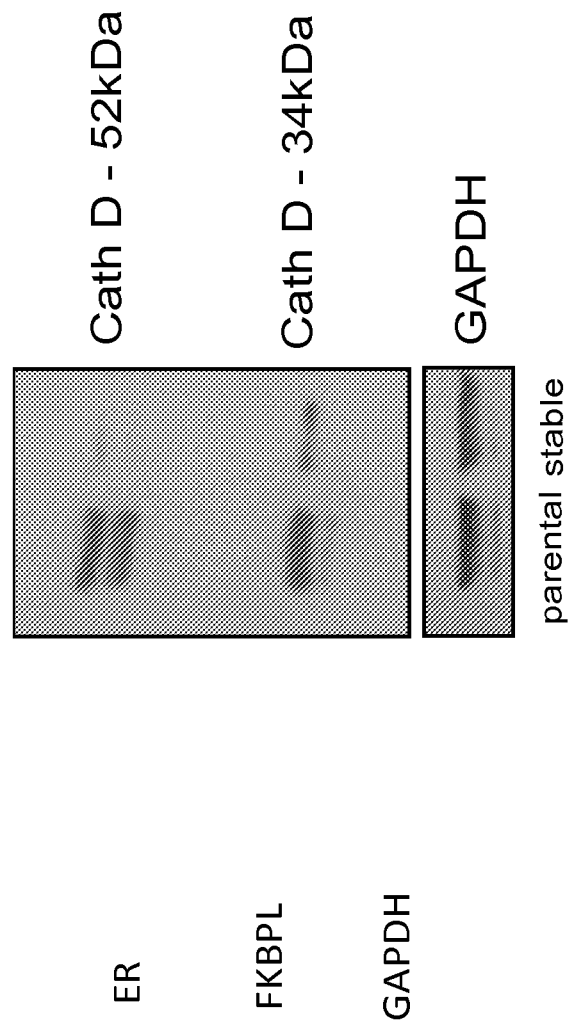
Figure 7C:
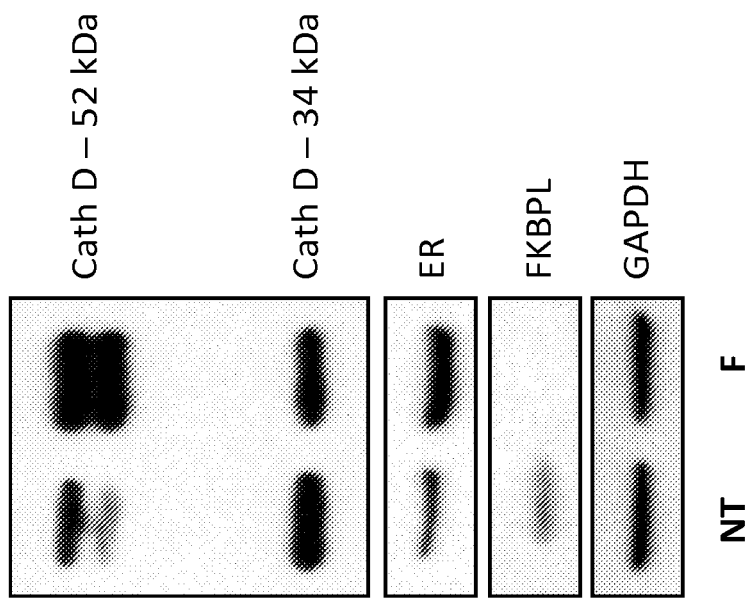
Figure 8:
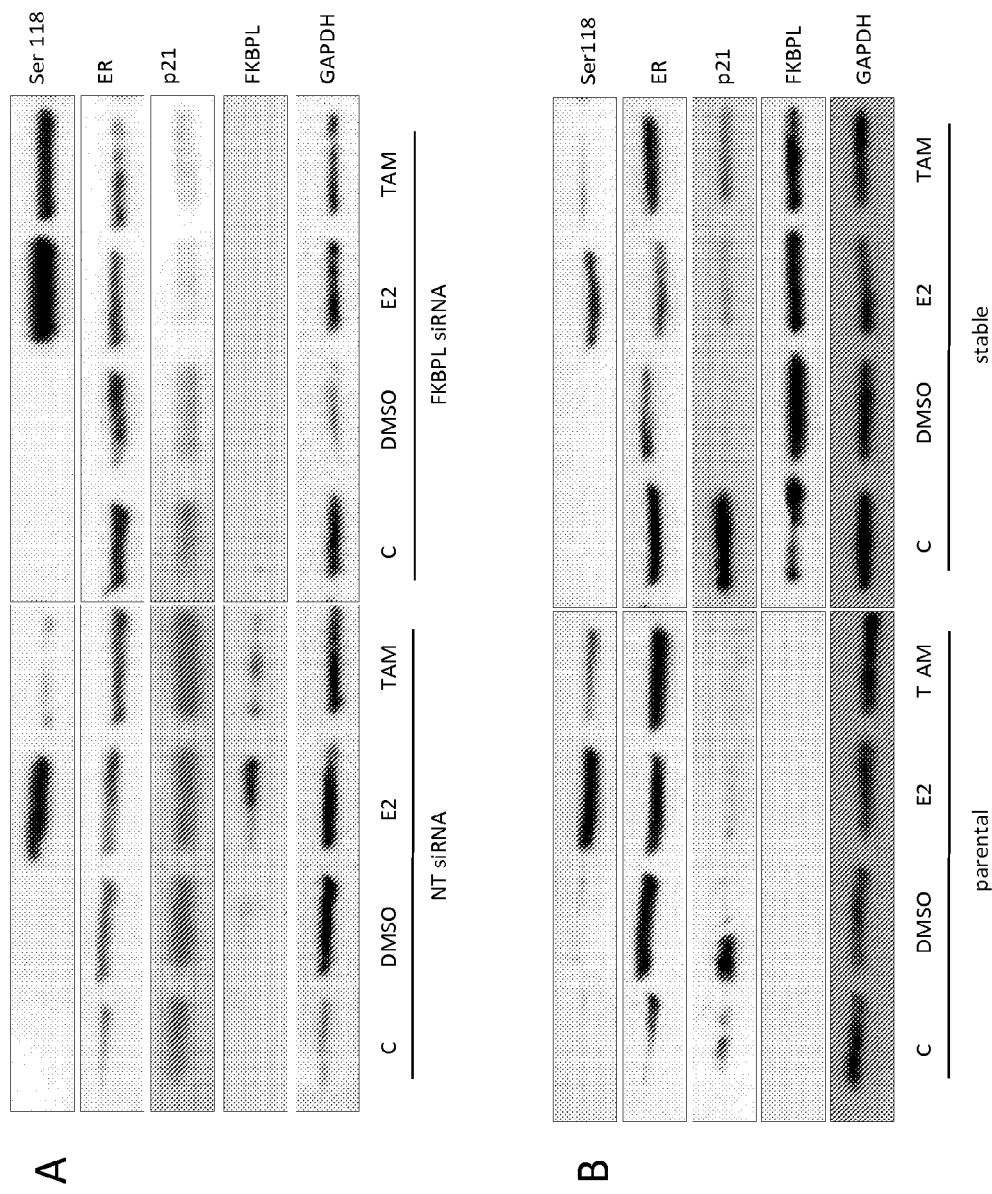
Figure 9:
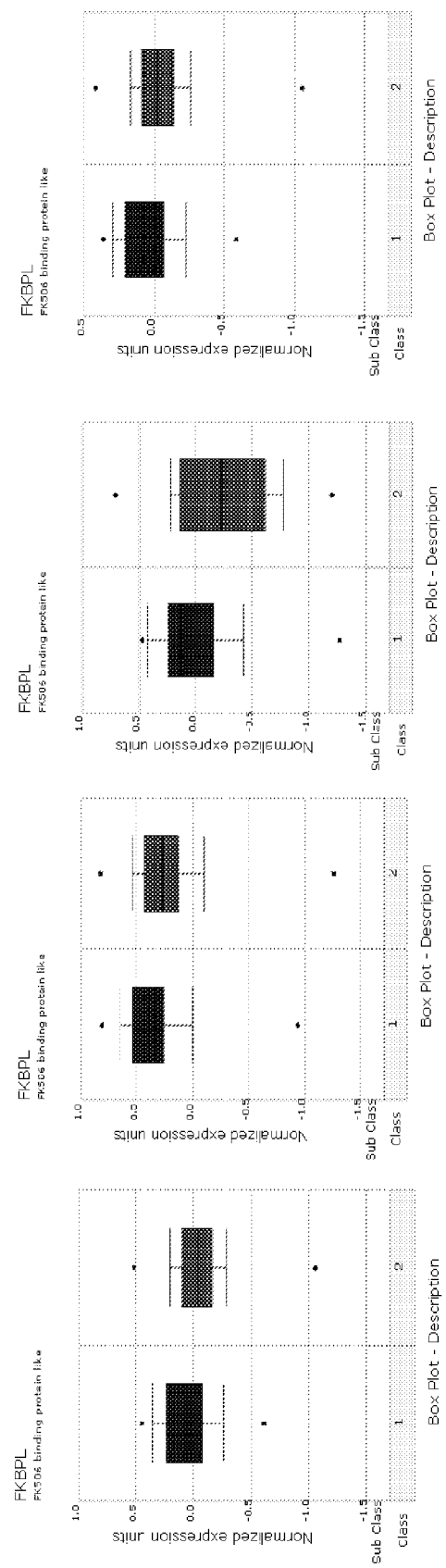
Figure 10:
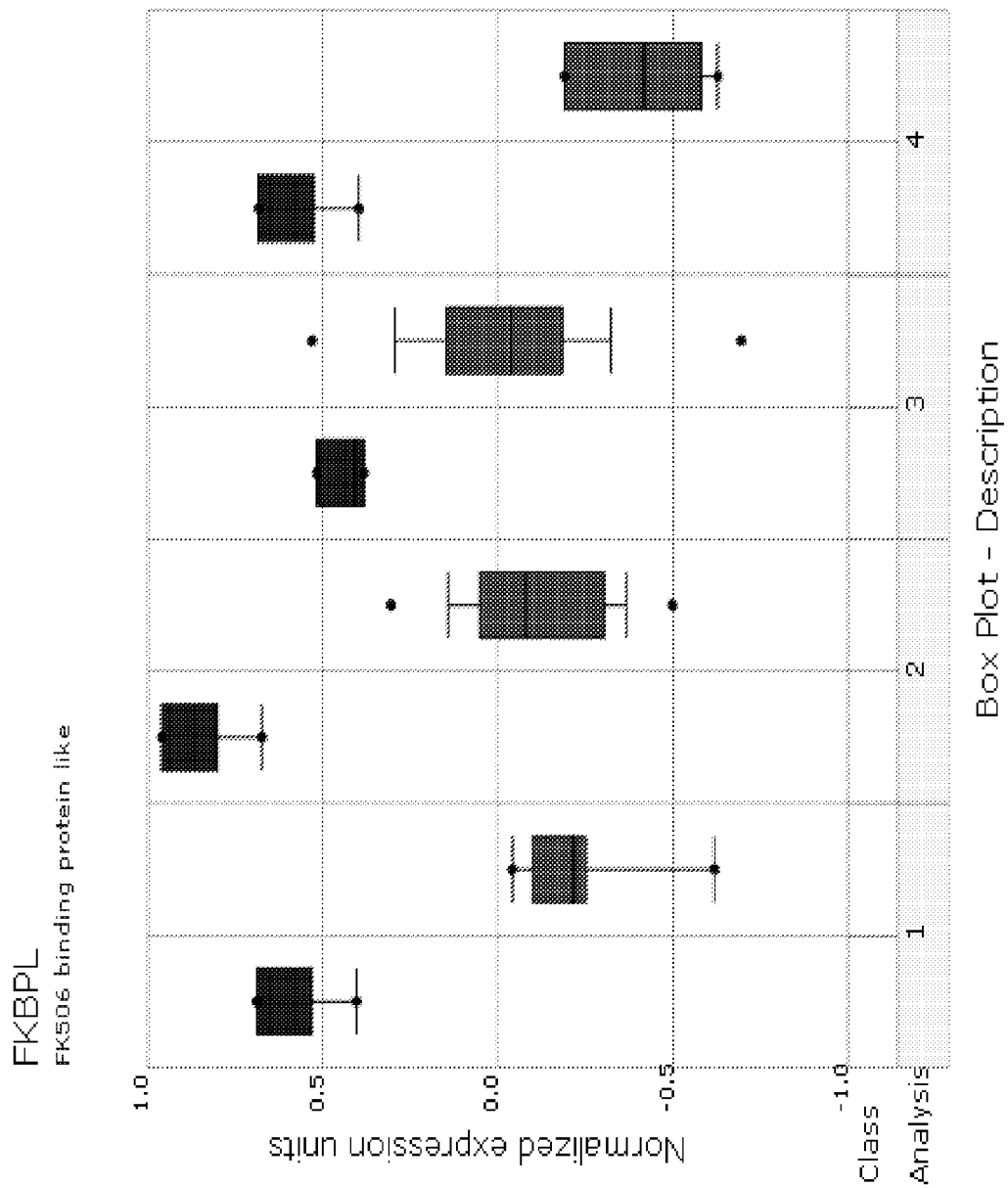

FIG. 5A shows dependence on oestrogen renders FKBPL-overexpressing cells more sensitive to tamoxifen; FIG. 5B shows that FKBPL overexpression sensitizes MCF-7 cells to fulvestrant; FIG. 5C shows correlation between tamoxifen IC5O and FKBPL protein expression in breast cancer cell lines and; FIG. 5D shows FKBPL knockdown by SiRNA confers resistance to tamoxifen and fulvestrant in MCF-7;

FIG. 6A shows (SEQ ID No 5) FKBPL has putative oestrogen responsive elements within its promoter (underlined and bold) and FIG. 6B that FKBPL is upregulated in response to oestrogen;

FIGS. 7A and B show FKBPL over-expressing cells exhibit decreased levels of oestrogen receptor and cathepsin D while FKBPL knockdown causes increased expression of oestrogen receptor and cathepsin D, FIG. 7C shows FKBPL repression in MCF7 cells increases levels of ER and the ER-responsive gene, cathepsin D;

FIG. 8 shows that oestrogen receptor phosphorylation is increased in FKBPL knock down cells and decreased in FKBPL over-expressing cells;

FIG. 9 illustrates microarray analysis of FKBPL levels in ER+VC versus ER−ve breast tissue and cell lines wherein Study 1 is: Ivshina Breast Experiment Type: mRNA Analysis: Breast Carcinoma-Estrogen Receptor Status; Class 1: Negative (34); Class 2: Positive (211); T-test: P-value: 0.008; Study 2 is Bittner Breast Experiment Type: mRNA Analysis: Breast Carcinoma-Estrogen Receptor Status, Class 1: Negative (78); Class 2: Positive (154); T-test: P-value 0.009; Study 3 is Neve CellLine Experiment type: mRNA Analysis: Breast Cell Line-Estrogen Receptor Status, Class 1: Negative (32), Class 2: Positive (18); T-test: 2919 P-value: 0.006; Study 4 is Miller Breast Experiment Type: mRNA Analysis: Breast Carcinoma-Estrogen Receptor Status, Class 1: Negative (34); Class 2: Positive (213); T-test: P-value: 0.01; and FIG. 10 illustrates that FKBPL levels fall as tumours progress or when compared to normal tissue, wherein Study 1 is Bredel Brain 2 Experiment Type: mRNA Analysis: Brain-Type, Class 1: Normal Brain (4); Class 2: Oligodendroglioma (8); T-test: 8.859 P-value: 6.9E-6; Study 2 is Bredel Brain 2 Experiment Type: mRNA Analysis: Brain Type, Class 1: Normal Brain (4); Class 2: Glioblastoma (31); T-test: 13.175 P-value: 1.4E-5; Study 3 is Liang Brain Experiment Type: mRNA Analysis: Brain-Type, Class 1: Normal Brain (3); Class 2: Glioblastoma Multiforme (30); T-Test: 7.464 P-value: 1.8E-5; Study 4 is Bredel Brain 2 Experiment Type: mRNA Analysis: Brain-Type, Class 1: Normal Brain (4); Class 2: Astrocytic Tumor (5); T-test: 9.627 P-value: 3.3E-S.

Figure 3:
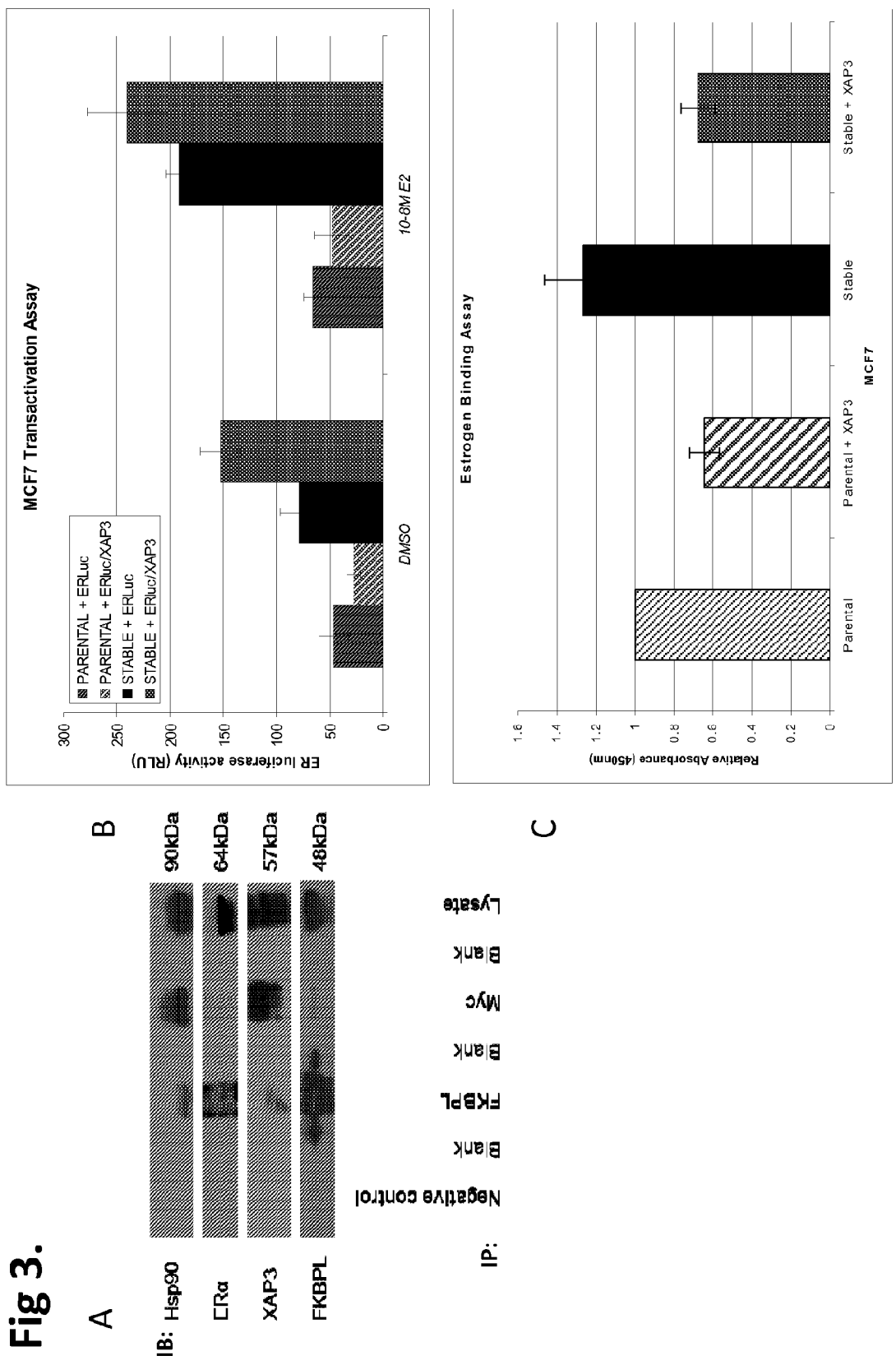
FIG. 3 illustrates FKBPL and XAP3 interact within ER complex and overexpression of these proteins affects ER transactivity and coactivator binding.

FKBPL was determined as part of the steroid receptor molecular complex along with oestrogen receptor and Hsp90 (FIGS. 1a & b). Furthermore, FKBPL was determined to co-localise with tubulin, strongly supporting the role of FKBPL in retrograde transport of hormone receptor complexes along microtubules (FIG. 1c). XAP3 and USP19 have been identified and confirmed as proteins which also interact with FKBPL (FIG. 2a-d). Moreover, XAP3 interacts in a complex with ER and FKBPL (FIG. 3a) and XAP3 overexpression affects ER transactivity and coactivator binding (FIGS. 3b & c). ER+ve MCF-7 breast cancer cells, stably overexpressing FKBPL, become dependent on oestrogen for their growth, and even in the presence of oestrogen, FKBPL overexpression inhibits the clonogenic potential of ER+ve MCF-7 cells (FIGS. 4a & b). This is indicative that breast tumours overexpressing FKBPL would be highly sensitive to aromatase inhibitors, which act by lowering circulating levels of estrogen.

Dependence on oestrogen renders FKBPL-overexpressing cells up to 90% more sensitive to tamoxifen and up to 99% more sensitive to fulvestrant (FIGS. 5a & b). These responses are not clonal, as several independent FKBPL overexpressing clones displayed the same phenotype.

A preliminary study using cell lines of differing tamoxifen sensitivity indicates a correlation with FKBPL levels (FIG. 5c). Knock-down of FKBPL in wild-type MCF-7 cells, using a targeted siRNA approach, dramatically increased the resistance of these cells to tamoxifen (FIG. 5d), supporting a role for FKBPL as a determinant of response to endocrine therapies.

Figure 6:
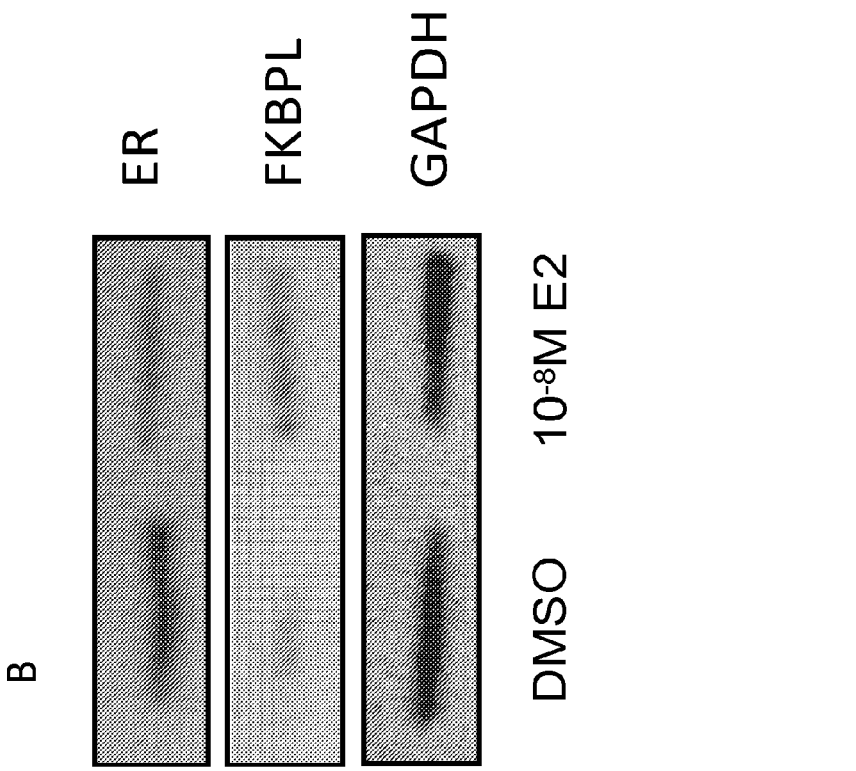

The inventors have shown that FKBPL has putative oestrogen responsive elements within its promoter and is upregulated in response to oestrogen (FIG. 6—promoter sequences with oestrogen receptor binding sites are marked thereon.). This suggests that FKBPL itself is an oestrogen responsive gene.

Further, the inventors have determined that as FKBPL levels increase in response to oestrogen, ER levels fall. This implicates FKBPL in the stabilisation of ER.

The inventors have demonstrated that FKBPL over-expressing cells exhibit decreased levels of ER suggesting that FKBPL affects ER stability (FIG. 7a). This is supported by a decrease in the levels of cathepsin D, an oestrogen-responsive gene critical to breast cancer growth, survival and invasion (FIG. 7b).

Cathepsin D down-regulation might explain the decreased cell growth observed in the FKBPL stably overexpressing cells. Furthermore, knockdown of FKBPL using an siRNA approach increased ER and cathepsin D levels (FIG. 7c). These data strongly support a role for FKBPL protein in controlling the stability of ER protein, as mRNA levels were not affected.

Without wishing to be bound by theory, the inventors propose that in addition to FKBPL's role in stabilising ER levels, FKBPL over-expression also has an impact on other pathways affecting tamoxifen sensitivity, including the stabilisation (together with Hps90) of the cyclin dependent kinase inhibitor, p21 (Jascur et al., 2006). In support of the present invention, the inventors have determined a dramatic fall in p21 levels when FKBPL is knocked down with a targeted siRNA (see FIG. 8a).

A loss of p21's cyclin dependent kinase inhibitory property resulted in hyperphosphorylation of ER at S118, with subsequent increased expression of oestrogen receptor-regulated genes.

The inventors have shown that ER phosphorylation is increased in FKBPL knock down cells and decreased in FKBPL over-expressing cells (FIGS. 8a & b). Together, these data support a model in which low levels of FKBPL leads to low levels of p21, hyperphosphorylation of ER and a growth-inducing phenotype.

This is supported by the inventors data shown in FIGS. 5d and 8a. By contrast, high levels of FKBPL stabilises p21, reducing ER phosphorylation, abrogating tamoxifen-induced agonist potency and so increase sensitivity to the drug (see data in FIGS. 5a and 8b).

Using a DNA microarray-based transcriptomic approach, the inventors have determined differentially expressed genes within the ligand-independent ER signalling pathway and in addition, ADAM9, a gene previously shown to predict for sensitivity to tamoxifen, independently of ER status is potentially up-regulated by FKBPL (Sieuwerts et al, 2005).

Finally, analysis by the inventors has revealed that FKBPL levels fall as tumours progress or when compared to normal tissue (FIGS. 9 and 10).

EXAMPLES

Example 1

FKBPL Interacts with the Hsp90/ER Molecular Chaperone Complex

Since FKBPL contains TPR (tetratricopeptide repeat) domains in its C-terminus and these domains are known to bind the molecular steroid chaperone, Hsp90, this experiment assessed if FKBPL could bind Hsp90 and the steroid receptor, ER, along with other components of this complex.

To assess endogenous interactions between FKBPL and the Hsp90/ER complex using coimmunoprecipitation, parental and FKBPL-overexpressing stable MCF7 (ER+) cells were plated into T75 flasks and incubated for 24 h. Cells were lysed in 500 µl lysis buffer (20 mM Tris HCl pH 7.4, 1% Igepal, 12 mM sodium deoxycholate, 0.1% SDS, 10 mM sodium Molybdate, 1 complete EDTA-Free tablet-protease inhibitor). Pre-cleared lysates were incubated with antibody bound Protein G-Sepharose beads (Cancer Research, UK) at 4° C. overnight. The beads were washed 5 times in lysis buffer, suspended in 50 µl 2× Laemmli buffer and heated at 100° C. for 10 mins. Samples were subjected to SDS-PAGE electrophoresis using the XCell Surelock Mini-cell system (Invitrogen), transferred onto nitrocellulose membranes, blocked for 1 h at room temperature with 1% skim milk blocking solution and probed with anti-FKBPL rabbit polyclonal (ProteinTech, Cat no. 10060-1-AP) at a dilution of 1:2000, anti-ER alpha rabbit monoclonal (Millipore, Cat no. 07-662) at a dilution of 1:1000 and GAPDH rabbit monoclonal (Sigma, Cat no. G9545) at a dilution of 1:5000. The blot was then probed with anti-rabbit IgG HRP-linked whole secondary antibody (GE Healthcare, Cat no. NA934V) at a dilution of 1:10000. Antibody binding was detected using Supersignal West Pico Chemiluminescent Substrate (Pierce, Cat no. 34080). DU145 cells were plated on chamber slides, fixed in 4% paraformaldehyde for 20 min at room temperature, washed with ice-cold PBS and permeabilized with 2% Bovine Serum Albumin (BSA) containing 0.1% Triton-X 100 for 20 min at room temperature. FKBPL was visualized with an anti-FKBPL rabbit polyclonal IgG (dilution 1:50) (ProteinTech, Cat no. 10060-1-AP) with Alexa Fluor® goat anti-rabbit (GAR) 488 (Invitrogen, Cat no. A-11008) was used as secondary antibody; tubulin was visualized with an anti-α-Tubulin mouse monoclonal (1:500) (Sigma, Cat no. T6074) and Alexa Fluor® donkey anti-mouse (DAM) 594 (Invitrogen, Cat no. A-21203) was used as a secondary antibody (dilution 1:250). Negative controls were also analysed, to ensure that the secondary antibodies did not bind non-specifically. Slides were visualised using a Leica Confocal System TCS Sp2, (Leica, Germany). A ×40 magnification oil immersion Plan Apochromatic objective was employed.

The results of the experiments are shown in FIG. 1. FKBPL, Hsp90 and ER are present in the whole cell lysate of MCF7 cells. Both Hsp90 and ER can be immunoprecipitated from MCF7 cells using the FKBPL antibody therefore demonstrating that these proteins interact in breast cancer cells.

Example 2

FKBPL Interacts with the Ubiquitin-Related Proteins, XAP3 and USP19 in Yeast and Mammalian Cells To determine other FKBPL interacting proteins, the inventors used the ProQuest Yeast Two-Hybrid System (Invitrogen, Cat no. 10835-015) to screen a human fetal brain pPC86/cDNA library. FKBPL was cloned into the pDBLeu plasmid 'in-frame' with the GAL4 binding domain according to manufacturer's instructions. MaV203 yeast cells were aliquoted into two 250 µl volumes and to each tube 20 µg of pDBLeu/FKBPL and 20 µg pPC86/cDNA library plasmids were added and mixed well by swirling tubes. To each tube, 1.5 ml PEG/LiAc was added and mixed well by swirling. Tubes were incubated for 30 minutes in a 30° C. waterbath, swirling tubes every 10 minutes. To each tube, 88 µl of fresh DMSO was added and mixed by swirling. Cells were heat shocked for 20 minutes in a 42° C. waterbath, swirling tubes occasionally. Tubes were centrifuged at 1800 rpm for 5 minutes and the supernatant discarded. Each pellet was resuspended in 8 ml 0.9% NaCl, then combined into one tube. To enable estimation of the total number of transformants, 100 µl was removed and diluted 1:10, 1:100 and 1:1000 in 0.9% NaCl. 100 µl of each dilution was plated onto a 10 cm SC-Leu-Trp plate then incubated at 30° C. for 72 hours. The remaining transformation mixture was plated in 400 µl aliquots onto forty 15 cm SC-Leu-Trp-His+10 mM 3AT plates and incubated at 30° C. for 6 days. Any colonies that grew were streaked onto a 10 cm SC-Leu-Trp plate and incubated for 2-3 days at 30° C. Following incubation, this master plate was replica plated onto selection plates in the following order—1. YPAD containing a nitrocellulose membrane, 2. SC-Leu-Trp-Ura, 3. SC-Leu-Trp-His+10 mM 3AT (immediately replica clean) then 4. SC-Leu-Trp+0.2% 5FOA (immediately replica clean). All plates were incubated for 24 hours at 30° C. After 24 hours the YPAD plate was removed and the X-Gal assay was performed. All other plates were replica cleaned and incubated at 30° C. for a further 48 hours. The growth of interacting proteins were compared with the known controls present on each plate but generally a positive interaction was assessed using the following criteria—blue colonies with X-Gal assay, colony growth on SC-Leu-Trp-Ura and SC-Leu-Trp-His+10 mM 3AT plates and no growth on SC-Leu-Trp+0.2% 5FOA. The plasmid DNA was extracted from yeast cells by alkaline lysis and electroporated into ELECTROMAX DH10B E. coli cells using a Gene Pulser Cuvette (0.1 cm electrode) (BioRad) voltage (2.5 kV), capacitance (25 µF) and resistance (100Ω). To selectively isolate pPC86/potential positive clones, cells were plated onto LB plates containing 50 µg/ml ampicillin and incubated for 16 hours at 37° C. Plasmid DNA was then isolated using standard alkaline lysis method.

Results are shown in FIGS. 2 A & B. Sequencing using plasmid specific primers and BLAST sequence alignments (www.ncbi.nlm.nih.gov) identified these interacting proteins as XAP3 and USP19. XAP3 produced blue colonies with X-Gal assay, minimal colony growth on SC-Leu-Trp-Ura, good colony growth on SC-Leu-Trp-His+10 mM 3AT plates and no growth on SC-Leu-Trp+0.2% 5FOA, identifying this protein as strong interactor. USP19 produced pale blue colonies with X-Gal assay, no colony growth on SC-Leu-Trp-Ura, good colony growth on SC-Leu-Trp-His+10 mM 3AT plates and slight growth on SC-Leu-Trp+0.2% 5FOA, identifying this protein as weak interactor.

In order to confirm the interactions detected using the yeast two-hybrid system and determine that the interaction can take place in a biologically relevant model, the Checkmate Mammalian Two-Hybrid System (Promega, Cat no. E2440) was used. Full length FKBPL and a variety of FKBPL mutants were cloned 'in-frame' into pBIND plasmid according to manufacturer's instructions. XAP3 and USP19 were cloned 'in-frame' into pACT plasmid according to manufacturer's instructions. $2 \times 10^4$ L132 cells were plated in triplicate into a 96 well plate for each transfection condition and incubated overnight at 37° C. with MEM containing 10% FCS. FKBPL, XAP3 and USP19 plasmids were transfected into cells using Lipofectamine Plus (Invitrogen, Cat no.) and incubated at 37° C. for 24 h. The plate was allowed to equilibrate to room temperature then 75 µl room temperature Dual-Glo Luciferase Reagent (Promega, Cat no. E2920) was added to each well, mixed thoroughly and wrapped in tinfoil. After 15 minutes incubation at room temperature, the Firefly luminescence was measured using a GENios platereader (Tecan). 75 µl room temperature Dual-Glo Stop & Glo Reagent (Promega, Cat no. E2920) was added to each well, mixed thoroughly and wrapped in tinfoil. After 15 minutes incubation at room temperature, the Renilla luminescence was measured.

Results are shown in FIGS. 2 C & D. Renilla luminescence was used to correct for plasmid transfection efficiency. Following correction, increased firefly luminescence over self-activations controls indicated a positive interaction between the proteins. Both XAP3 and USP19 were confirmed as true FKBPL interactors with a 20-fold and 10-fold induction of firefly luminescence, respectively. Deletion mapping demonstrated that the interaction between FKBPL and XAP3 was abrogated in FKBPLΔ287 mutant constructed so that FKBPL contained a single point mutation in a conserved, positively charged amino acid (carboxylate clamp) known to be essential for TPR interactions. Furthermore, removal of 149 amino acids from the end of FKBPL ie FKBPLΔ200 also abrogated any interaction with XAP3. These results identify that the region of FKBPL from 200-349 amino acids is essential for interaction with XAP3. Deletion mapping also identified the region spanning amino acids 1-200 as essential for binding of FKBPL to USP19.

Example 3

FKBPL and XAP3 Interact within the ER Complex and Overexpression of these Proteins Affects ER Transactivity and Coactivator Binding To assess whether XAP3 was also present in the FKBPL/Hsp90/ER complex, FKBPL stable 3.1D2 cells transiently transfected with pcDNA3.1-Myc/XAP3 were grown to 75% confluency in two T175 flasks. Spent media was removed and cells washed twice with ice-cold PBS. To each plate 500 µl RIPA lysis buffer was added and incubated for 1 h at 4° C. with rotation before being pelleted by centrifugation for 10 min at 4° C. 80 µl of the supernatant was removed and placed in a clean eppendorf together with 20 µl 5× Reducing lane marker sample buffer (Pierce, Cat no. 39000), boiled for 10 m and stored at −20° C. to be used as a positive control. 100 µl of Protein G-sepharose beads (Cancer Research, UK) were placed in an eppendorf, centrifuged at 2500 rpm for 1 min, and supernatant removed. The beads were then washed three times with 300 µl of lysis buffer and centrifuged at 2500 rpm for 1 min. The supernatant was added to pre-washed beads and incubated at 4° C. with rotation overnight to pre-clear the lysate. Simultaneously, the beads-antibody matrices were set up. Each antibody was diluted in 500 µl of PBS and 100 µl of pre-washed Protein G-sepharose beads and incubated at 4° C. with rotation overnight. Following incubation, the beads-antibody matrices were centrifuged at 2500 rpm for 1 min, the supernatant discarded and beads washed twice with ice-cold lysis buffer. The lysate was centrifuged at 2500 rpm for 20 min and the supernatant divided equally between the IP beads-antibody matrices and incubated at 4° C. with rotation overnight. Following incubation the IPs were centrifuged at 2500 rpm for 1 min, the supernatant discarded and washed three times with 500 µl of ice-cold lysis buffer, and twice with ice cold PBS, centrifuging each time as before and discarding the supernatant. The final supernatant was aspirated off with a fine needle. The samples were resuspended in 50 µl 5× Reducing lane marker sample buffer diluted 1:5 with lysis buffer, heated at 100° C. for 5 min and centrifuged. The membrane was immunoblotted for the following proteins; anti-FKBPL rabbit polyclonal (ProteinTech, Cat no. 10060-1-AP) at a dilution of 1:1000, anti-ER alpha rabbit monoclonal (Millipore, Cat no. 07-662) at a dilution of 1:1000, anti-Hsp90 mouse monoclonal (BD biosciences, Cat no. 610419) at a dilution of 1:1000 and anti-Myc mouse monoclonal (Invitrogen, Cat no. R95025) at a dilution of 1:5000. The blot was then probed with anti-rabbit IgG HRP-linked whole secondary antibody (GE Healthcare, Cat no. NA934V) or anti-mouse IgG HRP-linked whole antibody secondary (GE Healthcare, Cat no. NA931V) at a dilution of 1:10000. Antibody binding was detected using Supersignal West Pico Chemiluminescent Substrate (Pierce, Cat no. 34080).

To assess the ability of FKBPL and XAP3 to affect binding of ER to oestrogen response elements and therefore transactivation of ER responsive genes, $2 \times 10^4$ cells/well (96-well plate) parental MCF7 and FKBPL stable cells (3.1D2) were plated in triplicate for all conditions in phenol red-free DMEM containing 10% charcoal stripped fetal calf serum and incubated at 37° C. for 24 hours. Medium was carefully removed and 50 µl phenol red-free DMEM (serum free) added to each well (70 µl to non-transfected controls). Cells were transfected with an ERE-luciferase reporter plasmid (pGL2-ERE-TATA-LUC)+/−XAP3 plasmid using Lipofectamine Plus (Invitrogen, Cat no. P/N50470 and 10964-021) and optimized conditions (0.06 µg DNA, 0.2 µl Plus reagent, 0.3 µl lipofectamine per well), 20 µl of transfection mix was added to each well and incubated for 5 h. Following incubation, transfection mix was replaced with 50 µl phenol red-free DMEM containing 10% charcoal stripped fetal calf serum containing $10^{-8}$ M E2 or 0.1% (v/v) DMSO and incubated for 24 h. 50 µl Dual-Glo Luciferase reagent (Promega, Cat no. E2920) was added and mixed gently by pipetting up and down. The plate was covered with tinfoil and incubated at room temperature for 15 mins then firefly luminescence was measured using the GENios platereader (Tecan). 50 µl Stop and Glo reagent (Promega, Cat no. E2920) was added and mixed gently by pipetting up and down, covered with tinfoil and incubated at room temperature for 15 mins then *Renilla* luminescence was measured as before.

To determine whether FKBPL and XAP3 can affect the ability of ER to bind its coactivators, the NR Peptide ERalpha ELISA (Active Motif, Cat no. 49096) was used. This assay allows the specific capture of ligand-activated ER alpha and evaluates the agonist/antagonist effects of compounds on the activation of ER alpha. A 96-well plate is coated with a sequence optimized peptide containing the consensus binding motif (LXXLL) of ER alpha co-activators. 50 µg nuclear lysates from parental or stable MCF7 cells were added to a well along with the test compound (25 µM 17-β-estradiol or 25 µM tamoxifen). The plate was sealed with adhesive cover and incubated at room temperature for 1 h on a rocking platform (100 rpm). Wells were washed 3 times with 200 µl 1× Wash Buffer. 50 µl of diluted ER primary was added to all wells. Samples were incubated and washed as in previous step. 50 µl of diluted secondary antibody was added to all wells and incubated as before. Wells were washed 4 times with 200 µl 1× Wash Buffer. 100 µl Developing Solution was added and incubated for 2-5 minutes at room temp wrapped in tinfoil. 100 µl Stop Solution was added (blue colour should turn yellow). Absorbance was read on a spectrophotometer within 5 minutes at 450 nm.

Coimmunoprecipitations determined that XAP3 does interact in a complex with FKBPL/Hsp90/ER. Results shown in FIG. 3A. This is the first description of an interaction between these proteins. Furthermore, in both oestrogen-depleted (DMSO) and oestrogen-supplemented (E2) medium, overexpression of FKBPL enhanced ERα mediated transcription of the oestrogen response element-driven luciferase reporter and the presence of XAP3 further increased this effect. Results are shown in FIG. 3B. Furthermore, FKBPL overexpression significantly enhanced the ability of ER to bind the LXXLL coactivator sequence ($p=0.0127$). However, overexpression of XAP3 inhibited this effect. These results suggest that XAP3 itself may act as an ER coactivator and therefore increased presence of XAP3 may block coactivator binding sites on ER and prevent binding to coactivator sites on the ELISA plate. Results are shown in FIG. 3C. Together these data suggest that XAP3 may co-operate with FKBPL in the modulation of ER signalling.

Example 4

FKBPL Overexpression Sensitizes MCF7 Cells to Oestrogen Deprivation and Slows the Growth of Breast Cancer Cells In order to determine the cellular affects of FKBPL overexpression on breast cancer cells, MCF7 cells were engineered to constitutively overexpress FKBPL (3.1D2, 3.1D3 and 3.1D9) and assays performed to assess their clonogenic potential and cell growth under various culture conditions; MCF7 cells served as parental controls.

For oestrogen deprivation studies, 3.1D2 and parental control cells were plated at a density of 500 and 1000 cells/well in a 6-well plate containing phenol red-free DMEM+10% charcoal-stripped FCS and incubated at 37° C. for 24 h. The medium was replaced with phenol red-free DMEM+10% charcoal-stripped FCS containing DMSO as vehicle control or $10^{-8}$ M 17-β-estradiol (Sigma, Cat no. E2758) and incubated under normal conditions for 16 days. For growth assays, $2 \times 10^5$ MCF7 parental or FKBPL stable cells were seeded into 35 mm dishes with complete DMEM and incubated at 37° C. for 24 h. Cell growth was monitored at 24 h intervals using the trypan blue exclusion assay.

MCF-7 breast cancer cells, stably overexpressing FKBPL (3.1D2), become dependent on oestrogen for their growth, and even in the presence of oestrogen, FKBPL overexpression inhibits the clonogenic potential of MCF-7 cells (FIG. 4A). Furthermore, three independent FKBPL overexpressing MCF7 clones (3.1D2, 3.1D3 and 3.1D9) all demonstrate growth inhibition compared to parental controls over a 5 day timecourse (FIG. 4B).

Example 5

FKBPL Overexpression Sensitizes MCF7 Breast Cancer Cells to SERM and SERD Endocrine Therapies Cells were plated at a density of 500 and 1000 cells/well in a 6-well plate containing DMEM+10% FCS and incubated at 37° C. for 24 h. The medium was replaced with DMEM+10% FCS containing 1 µM tamoxifen (Sigma, Cat no. T5648) or 2.5 nM fulvestrant (Sigma, Cat no. I4409) and incubated under normal conditions for 16 days. In both experiments, colonies were fixed and stained with 0.4% Crystal Violet/70% methanol then counted.

FKBPL overexpression renders cells up to 90% more sensitive to the SERM (selective oestrogen receptor modulator), tamoxifen; these responses are not clonal, as several independent FKBPL overexpressing clones displayed the same phenotype (FIG. 5A). Furthermore, the amount of FKBPL protein overexpression in each clone correlated with the increased sensitivity to tamoxifen ($R^2=0.88$). In response to the SERD (selective oestrogen receptor down regulator), fulvestrant, overexpressing clones were up to 99% more sensitive than parental controls and again this response was not clonal (FIG. 5B). Correlation between FKBPL levels and sensitivity to fulvestrant was also identified ($R^2=0.81$).

Example 6

Endogenous FKBPL Protein Expression Correlates with Tamoxifen Sensitivity in Breast Cancer Cell Lines Protein lysates were isolated from MCF7 (ER+), MDA-MB-231 (ER−), T47D (ER+) and FKBPL overexpressing MCF7 cell lines, 3.1D2 and 3.1D9. The $IC_{50}$ of each cell line was determined as follows: cells were plated at a density of 500 and 1000 cells/well in a 6-well plate containing DMEM+ 10% FCS and incubated at 37° C. for 24 h. The medium was replaced with DMEM+10% FCS containing 0, 0.1, 0.25, 0.5, 1, 2.5, 5, 7.5, 10 µM tamoxifen (Sigma, Cat no. T5648) and incubated under normal conditions for 16 days. Colonies were fixed and stained with 0.4% Crystal Violet/70% methanol then counted.

The IC50 of each cell line was determined as the dose of tamoxifen required to inhibit clonogenic potential of cells by 50%. This in vitro study of breast cancer cell lines further expanded the evidence that higher endogenous FKBPL levels in breast cancer cell lines; T47D (FKBPL++), MCF7 (FKBPL+), MDA-MB-231 (FKBPL+/−) and FKBPL stable cell lines, 3.1D2 (FKBPL+++) and 3.1D9 (FKBPL+) correlated with increased sensitivity to tamoxifen ($R^2=0.93$) (FIG. 5C).

Example 7

Knockdown of FKBPL in MCF7 Cells Via a siRNA Targeted Approach Confers Resistance to Endocrine Therapies MCF7 cells were transfected with siControl non-targeting siRNA #1 (Dharmacon, Cat no. D-001210-01-20) or FKBPL targeted siRNA (Ambion, Cat no. 16104). Briefly, $1\times10^5$ MCF7 cells were seeded into 35 mm dishes and incubated at 37° C. for 24 h. To transfect, in one tube 6.4 µl of either siControl non-targeting siRNA or FKBPL targeted siRNA (2 µM) was added to 160 µl OptiMEM (Invitrogen) and in another tube 4 µl Oligofectamine (Invitrogen, Cat no. 12252-011) was added to 30 µl OptiMEM. Both tubes were incubated at room temperature for 5 min. Both tube contents were mixed and incubated at room temperature for 20 min. During incubation, 800 µl prewarmed complete DMEM was added to the cells then 200 µl transfection mix was added dropwise and the dishes incubated at 37° C. for 72 h. Cells were then plated at a density of 1000 and 2000 cells/well in a 6-well plate containing DMEM+10% FCS and incubated at 37° C. for 24 h. The medium was replaced with DMEM+10% FCS containing 1 µM tamoxifen (Sigma, Cat no. T5648) or 2.5 nM fulvestrant (Sigma, Cat no. I14409) and incubated under normal conditions for 16 days. In both experiments, colonies were fixed and stained with 0.4% Crystal Violet/70% methanol then counted.

Knock-down of FKBPL in wild-type MCF-7 cells, using a targeted siRNA approach, dramatically increased the resistance of these cells to tamoxifen and fulvestrant compared to the non-targeting controls (FIG. 5D). This further supports a role for FKBPL as a determinant of response to endocrine therapies.

Example 8

FKBPL is an Oestrogen Responsive Gene

To identify regions of the FKBPL promoter which ER may bind to and therefore regulate FKBPL expression, 2206 bp upstream from the transcription start site of FKBPL were selected and the WWW ProScan Program was used to predict possible binding sites for ER-α.

To determine whether FKBPL itself could be regulated by oestrogen, $2\times10^5$ MCF7 parental cells were seeded into 35 mm dishes with phenol red-free DMEM+10% charcoal stripped FCS and incubated at 37° C. for 24 h. The medium was replaced with phenol red-free DMEM+10% charcoal-stripped FCS containing DMSO as vehicle control or $10^{-8}$M 17-β-estradiol (Sigma, Cat no. E2758) and incubated for 24 h. Cells were lysed in 250 µl 2× laemmli buffer (Sigma) and subjected to SDS-PAGE electrophoresis using the XCell Surelock Mini-cell system (Invitrogen), transferred onto nitrocellulose membranes, blocked for 1 h at room temperature with 1% skim milk blocking solution and probed with FKBPL rabbit polyclonal (ProteinTech, Cat no. 10060-1-AP) at a dilution of 1:2000, ER rabbit monoclonal (Millipore, Cat no. 07-662) at a dilution of 1:1000 and GAPDH rabbit monoclonal (Sigma, Cat no. G9545) at a dilution of 1:5000. The blot was then probed with corresponding anti-rabbit IgG HRP-linked whole antibody secondary (GE Healthcare, Cat no. NA934V) or anti-mouse IgG HRP-linked whole antibody secondary (GE Healthcare, Cat no. NA931V) at a dilution of 1:10000. Antibody binding was detected using Supersignal West Pico Chemiluminescent Substrate (Pierce, Cat no. 34080).

Using ProScan, several Sp1 and ERE sites were identified in the promoter region of FKBPL suggesting that ER could bind these regions directly via ERE sites or indirectly using other transcription factors via Sp1 sites. FKBPL protein expression is upregulated by administration of $10^{-8}$M 17-β-estradiol suggesting that FKBPL is an oestrogen responsive gene. Furthermore, as FKBPL levels increase, ER levels decrease implicating FKBPL in the stabilisation of ER. Results are shown in FIG. 6.

Example 9

FKBPL Overexpression in MCF7 Cells Decreases Levels of ER and the ER-Responsive Gene, Cathepsin D In order to determine how FKBPL overexpression sensitizes breast cancer cells to endocrine therapies, protein expression of ER and ER-responsive genes were analysed.

Briefly, $2\times10^5$ MCF7 parental or FKBPL stable cells were seeded into 35 mm dishes with complete DMEM and incubated at 37° C. for 24 h. Cells were then lysed in 250 µl 2× laemmli buffer (Sigma). Samples were subjected to SDS-PAGE electrophoresis using the XCell Surelock Mini-cell system (Invitrogen), transferred onto nitrocellulose membranes, blocked for 1 h at room temperature with 1% skim milk blocking solution and probed with FKBPL rabbit polyclonal (ProteinTech, Cat no. 10060-1-AP) at a dilution of 1:2000, ER rabbit monoclonal (Millipore, Cat no. 07-662) at a dilution of 1:1000, cathepsin D mouse monoclonal (Abcam, Cat no. ab6313) at a dilution of 1:1000 and GAPDH rabbit monoclonal (Sigma, Cat no. G9545) at a dilution of 1:5000. The blot was then probed with corresponding anti-rabbit IgG HRP-linked whole antibody secondary (GE Healthcare, Cat no. NA934V) or anti-mouse IgG HRP-linked whole antibody secondary (GE Healthcare, Cat no. NA931V) at a dilution of 1:10000. Antibody binding was detected using Supersignal West Pico Chemiluminescent Substrate (Pierce, Cat no. 34080).

Compared to parental controls, FKBPL over-expressing cells exhibit decreased levels of ER and cathepsin D, an oestrogen-responsive gene critical to breast cancer growth, survival and invasion (FIGS. 7a & b).

Example 10

Knockdown of FKBPL in MCF7 Cells Via a siRNA Targeted Approach Causes an Increase in Er and Cathepsin D Levels MCF7 cells were transfected for 72 h with siControl non-targeting siRNA #1 (Dharmacon, Cat no. D-001210-01-20) of FKBPL targeted siRNA (Ambion, Cat no. 16104). Briefly, $1\times10^5$ MCF7 cells were seeded into 35 mm dishes and incubated at 37° C. for 24 h. To transfect, in one tube 6.4 µl of either siControl non-targeting siRNA or FKBPL targeted siRNA (2 µM) was added to 160 µl OptiMEM (Invitrogen) and in another tube 4 µl Oligofectamine (Invitrogen, Cat no. 12252-011) was added to 30 µl OptiMEM. Both tubes were incubated at room temperature for 5 min. Both tube contents were mixed and incubated at room temperature for 20 min. During incubation, 800 µl prewarmed complete DMEM was added to the cells then 200 µl transfection mix was added dropwise and the dishes incubated at 37° C. for 72 h. Cells were then lysed in 250 µl 2× laemmli buffer (Sigma). Samples were subjected to SDS-PAGE electrophoresis using the XCell Surelock Mini-cell system (Invitrogen), transferred onto nitrocellulose membranes, blocked for 1 h at room temperature with 1% skim milk blocking solution and probed with FKBPL rabbit polyclonal (ProteinTech, Cat no. 10060-1-AP) at a dilution of 1:2000, ER rabbit monoclonal (Millipore, Cat no. 07-662) at a dilution of 1:1000, cathepsin D mouse monoclonal (Abcam, Cat no. ab6313) at a dilution of 1:1000, and GAPDH rabbit monoclonal (Sigma, Cat no. G9545) at a dilution of 1:5000. The blot was then probed with corresponding anti-rabbit IgG HRP-linked whole antibody secondary (GE Healthcare, Cat no. NA934V) or anti-mouse IgG HRP-linked whole antibody secondary (GE Healthcare, Cat no. NA931V) at a dilution of 1:10000. Antibody binding was detected using Supersignal West Pico Chemiluminescent Substrate (Pierce, Cat no. 34080).

Knockdown of FKBPL using an siRNA targeted approach increased ER and cathepsin D levels further supporting a role for FKBPL in controlling stability of ER signalling pathway proteins (FIG. 7C).

Example 11

Phosphorylation Status of ER is Altered Following FKBPL Knockdown and Overexpression To study the effect of FKBPL overexpression on ERα phosphorylation, $5\times10^4$ MCF7 cells and 3.1D2 were plated in a 24 well dish with 500 µl complete DMEM. After 12 h the medium was aspirated and replaced with 500 µl phenol red-free DMEM supplemented with 10% charcoal stripped FCS. After 72 h serum starvation, $10^{-8}$M 17-β estradiol or 1 µM tamoxifen was added. The vehicle control for the addition of estradiol was DMSO and for tamoxifen was fresh media. For studies on effect of FKBPL knockdown on ERα phosphorylation, siRNA transfection was carried out as outlined in Example 10 with the exception that phenol red-free DMEM+ 10% charcoal stripped FCS medium was used instead of complete DMEM. Cell lysates were assayed 15 min post-addition of ligand and subjected to SDS-PAGE electrophoresis using the XCell Surelock Mini-cell system (Invitrogen), transferred onto nitrocellulose membranes, blocked for 1 h at room temperature with 1% skim milk blocking solution and probed with FKBPL rabbit polyclonal (ProteinTech, Cat no. 10060-1-AP) at a dilution of 1:2000, ER rabbit monoclonal (Millipore, Cat no. 07-662) at a dilution of 1:1000, phospho-ERα (Ser118) mouse antibody (Cell Signalling Technologies, Cat no. 9924) at a dilution of 1:1000, p21 mouse monoclonal (Upstate, Cat no. 05-345) at a dilution of 1:1000 and GAPDH rabbit monoclonal (Sigma, Cat no. G9545) at a dilution of 1:5000. The blot was then probed with corresponding anti-rabbit IgG HRP-linked whole antibody secondary (GE Healthcare, Cat no. NA934V) or anti-mouse IgG HRP-linked whole antibody secondary (GE Healthcare, Cat no. NA931V) at a dilution of 1:10000. Antibody binding was detected using Supersignal West Pico Chemiluminescent Substrate (Pierce, Cat no. 34080).

Results demonstrate that ER phosphorylation is increased in FKBPL knockdown cells and decreased in FKBPL over-expressing cells (FIGS. 8A & B). Furthermore, p21 levels are decreased compared to controls following FKBPL knockdown and increased in FKBPL stable cell line compared to controls Example 12

Genes Regulated by FKBPL Peptide Associated with ER Signalling in MDA-MB-231 Cells MDA-MB-231 cells were seeded onto chamber slides and incubated at 37° C. for 24 h. Treatment with 24mer FKBPL peptide was carried out for 18 h then cells were harvested in 1 ml RNA-STAT-60 (AMS Biotechnology, Cat no. CS-111) to enable total RNA isolation according to manufacturer's instructions. These RNA samples were analysed using Affymetrix Human Genome U133 Plus 2.0 arrays (Almac Diagnostics UK). Briefly, 50 ng of total RNA was amplified using the NuGEN™ Ovation™ RNA Amplification System V2. First-strand synthesis of cDNA was conducted using a unique first-strand DNA/RNA chimeric primer mix, resulting in cDNA/mRNA hybrid molecules. Following fragmentation of the mRNA component of the cDNA/mRNA molecules, second-strand synthesis was conducted and double-stranded cDNA generated using a unique DNA/RNA heteroduplex at one end. In the final amplification step, RNA within the heteroduplex was degraded using RNaseH, and replication of the resultant single-stranded cDNA was achieved through DNA/RNA chimeric primer binding and DNA polymerase enzymatic activity. The amplified single-stranded cDNA was purified using the Zymo Research Clean and Concentrator™-25 kit to allow for accurate quantitation of the cDNA and to ensure optimal performance during the fragmentation and labelling process. The single-stranded cDNA was assessed using a spectrophotometer in combination with the Agilent Bioanalyzer to ensure all samples were comparable. 3.75 µg of amplified single-stranded cDNA was fragmented and labelled using the FL-Ovation™ cDNA Biotin Module V2. The enzymatically and chemically fragmented product (50-100 nt) was labelled via the attachment of biotinylated nucleotides onto the 3'-end of the fragmented cDNA. This cDNA was added to the hybridisation cocktail in accordance with the NuGEN™ guidelines for hybridisation onto Affymetrix GeneChip® arrays. Following hybridisation for 18 hours at 45° C., the array was washed and stained on a GeneChip® Fluidics Station 450 using the appropriate fluidics script, before being inserted into the Affymetrix autoloader carousel and scanned using the GeneChip® Scanner 3000. The image files were assessed for proper grid alignment and image artefacts and the data was also assessed using Affymetrix QC measures. Background intensity, RawQ (Scanner Noise), and scaling factor were assessed for comparability between samples. Process control spike in probes (PolyA) and hybridisation control spike-in probes were assessed to ensure no problems with sample processing or hybridisation, and % Present calls were assessed to ensure adequate levels of expression data and ensure no potential outlying replicate chips. Hierarchical Clustering, Principal Components Analysis (PCA) and Multidimensional Scaling was then carried out to assess the suitability of data for further analysis (Almac Diagnostics). Following this analysis, samples were subjected to Gene Ontology Analysis, Upstream Sequence Analysis, Metacore Pathway Analysis to elucidate mechanisms.

Genes involved in ligand-independent ER signalling pathways were modulated following treatment with 24mer (Table 2). ADAM 9 was upregulated and has been shown to predict tamoxifen sensitivity independently of ER. This data implies that high levels of FKBPL regulate ER signalling.

TABLE 2

Genes differentially expressed following treatment with FKBPL 24mer peptide

| Gene Name | Fold Increase (+), Fold Decrease (−) |
| --- | --- |
| ADAM 9 | +1.84 |
| CREBBP | −1.68 |
| EGFR | −1.78 |
| HRAS | +1.98 |
| PDPK1 | +1.96 |
| PIK3R1 | +1.68 |
| SOS1 | −1.79 |
| RAF1 | −1.4 |

Although the invention has been shown and described with reference to particular examples, it will be understood by those skilled in the art that various changes in the form and details may be made therein without departing from the scope of the present invention.

The invention claimed is:

1. A method of characterizing a cancer tissue in a breast cancer subject as highly sensitive to anti-oestrogen agents comprising:

determining in a test biological sample of tissue from the breast cancer subject an expression level of at least one of FKBPL, a FKBPL variant, and a fragment FKBPL or an FKBPL variant;

comparing the expression level of at least one FKBPL, a FKBPL variant, a fragment FKBPL or FKBPL variant in the test sample to the expression level of at least one FKBPL, a FKBPL variant, a fragment FKBPL or FKBPL variant in a control sample;

determining whether there is a differential expression of FKBPL in the test sample as compared to the expression of FKBPL in the control sample;

characterizing the subject as having a tumour highly sensitive to anti-oestrogen agents when their breast tissue expresses an increased level of FKBPL compared to a normal control, or characterizing the subject as having a tumour that is not sensitive to anti-oestrogen agents when their breast tissue expresses a decreased level of FKBPL compared to a normal control; and administering an anti-oestrogen agent to the subject that is characterized as having a tumour highly sensitive to anti-oestrogen agents, or administering a treatment that does not modulate an oestrogen receptor to the subject that is characterized as having a tumour that is not sensitive to anti-oestrogen agents.

2. The method of claim 1 wherein determining the expression level of FKBPL comprises measuring the level of an expression product of a FKBPL encoding gene.

3. The method of claim 2 wherein the expression product is mRNA or a protein.

4. The method of claim 1 wherein the expression product is determined using an antibody or binding fragment thereof with binding specificity to FKBPL.

5. The method of claim 1 wherein FKBPL levels are assessed before treatment with any agent and the levels of FKBPL are qualitatively scored to predict outcome or potential response to treatment.

6. The method of claim 1 wherein the method further comprises the step of determining in the test biological sample the level of expression of at least one of an oestrogen receptor and a progesterone receptor in the tissue.

7. The method of claim 1 wherein the method further comprises determining the phosphorylation status of an oestrogen receptor in the tissue.

8. The method of claim 1 wherein the method further comprises obtaining from the subject the control sample prior to the on-set of cancer.

9. The method of claim 1 further comprising the step of obtaining from the subject, prior to the start of the treatment resuming for the cancer, the control sample to be used in the method.

10. The method of claim 1 wherein the step of administering a treatment comprises providing a treatment to prevent metastasis.

11. The method of claim 1 wherein the anti-oestrogen agents are selective oestrogen receptor modulators, selective oestrogen receptor downregulators or aromatase inhibitors.

* * * * *

UNITED STATES PATENT AND TRADEMARK OFFICE
CERTIFICATE OF CORRECTION

PATENT NO. : 9,110,063 B2
APPLICATION NO. : 13/265223
DATED : August 18, 2015
INVENTOR(S) : Tracy Robson et al.

It is certified that error appears in the above-identified patent and that said Letters Patent is hereby corrected as shown below:

Specification

| Patent | Application File |
| --- | --- |
| Column 2, Lines 51-52 | Replace "Accession number" with -- Accesion number -- |
| Column 10, Line 60 | Replace "(fulvestrant)" with -- (fluvestrant) -- |

Signed and Sealed this
Twenty-first Day of June, 2016

Michelle K. Lee
*Director of the United States Patent and Trademark Office*